US007235713B2

(12) United States Patent
Ishitani et al.

(10) Patent No.: US 7,235,713 B2
(45) Date of Patent: Jun. 26, 2007

(54) POTASSIUM CHANNEL STRESS-RELATED PROTEINS AND METHODS OF USE IN PLANTS

(75) Inventors: Manabu Ishitani, Cary, NC (US); Ruoying Chen, Apex, NC (US); Nocha van Thielen, Chapel Hill, NC (US); Oswaldo da Costa e Silva, Cary, NC (US)

(73) Assignee: BASF Plant Science GmbH, Ludwigshafen (DE)

( * ) Notice: Subject to any disclaimer, the term of this patent is extended or adjusted under 35 U.S.C. 154(b) by 435 days.

(21) Appl. No.: 10/169,038

(22) PCT Filed: Dec. 22, 2000

(86) PCT No.: PCT/US00/35356

§ 371 (c)(1),
(2), (4) Date: Nov. 18, 2002

(87) PCT Pub. No.: WO01/45495

PCT Pub. Date: Jun. 28, 2001

(65) Prior Publication Data
US 2005/0014265 A1    Jan. 20, 2005

Related U.S. Application Data

(60) Provisional application No. 60/171,745, filed on Dec. 22, 1999.

(51) Int. Cl.
*A01H 5/00* (2006.01)
*A01H 5/10* (2006.01)
*C12N 15/29* (2006.01)
*C12N 15/82* (2006.01)

(52) U.S. Cl. .................. 800/298; 435/320.1; 536/23.6; 800/289; 800/320

(58) Field of Classification Search ................ 800/287, 800/298
See application file for complete search history.

(56) References Cited

U.S. PATENT DOCUMENTS 6,635,803 B1 * 10/2003 Schroeder et al. .......... 800/278

FOREIGN PATENT DOCUMENTS

AU    5016499    4/2000
JP    11187878    7/1999

OTHER PUBLICATIONS

Ashley et al 2006, Journal of Experimental Botany 57(2): 425-436.*
Mäser et al 2001 Plant Physiology 126: 1646-1667.*
Bohnert H.J. and Jensen, R.G., "Strategies for engineering water-stress tolerance in plants", 1996, Trends in Biotech., 14:89-97.
Ehret, D.L. and Boyer, J.S., "Potassium Loss from Stomatal Guard Cells at Low Water Potentials", 1979, J. Experi. Bot. 30:225-234.
Fairbairn, D.J. et al., "Characterisation of two distinct HKT1-like potassium transporters from *Eucalyptus camaldulensis*", 2000, Plant Molec. Biol. 43:515-25.
Gaymard, F. et al., "Identification and Disruption of a Plant Shaker-like Outward Channel Involved in K+ Release into the Xylem Sap", 1998, Cell 94:647-55.
Girke, T., "Identification of a novel Δ6-acyl-group desaturase by targeted gene disruption in Physcomitrella patens" 1998, The Plant Journal 15:39-48.
Groves, J.T., "Peroxynitrite: reactive, invasive and enigmatic", 1999, Curr. Opin. Chem. Biol. 3(2):226-235.
Hirsch, R.E. and Sussman, M.R., "Improving nutrient capture from soil by the genetic manipulation of crop plants", 1999, Trends in Biotech., 17:356-361.
Hirsch, R.H., et al., "A Role for the AKT1 Potassium Channel in Plant Nutrition", 1998, Science 280:918-921.
Ichida, A.M. et al., "Expression of a Cs+-Resistant Guard Cell K+ Channel Confers Cs+-Resistant, Light-Induced Stomatal Opening in Transgenic Arabidopsis", 1997, The Plant Cell 9:1843-57.
Machuka, J. et al., "Sequence Analysis of Expressed Sequence Tags from an ABA-Treated cDNA library Identifies Stress Response Genes in the Moss Physcomitrella patens", 1999, Plant Cell Physiol. 40(4):378-387.
Munns R. et al., "Solute Accumulation in the Apex and Leaves of Wheat During Water Stress", 1979, Aust. J. Plant Physiol. 6:379-389.
Pastore, D. et al., "The Existence of the K+ Channel in Mitochondria", 1999, Journal of Biolog. Chem. 274(38):26683-90.
Quarrie SA, "New molecular tools to improve the efficiency of breeding for increased drought resistance", 1996, Plant Growth Reg. 20:167-178.
Roberts, S.K., "Regulation of K+ Channels in Maize Roots by Water Stress and Abscisic Acid", 1998, Plant Physiol. 116:145-53.
Ros R. et al., "Molecular determinants of the Arabidopsis AKT1 K+ channel ionic selectivity investigated by expression in yeast of randomly mutated channels", 1999, Physiologia Plantarum 105(3):459-68.
Serrano, R., "Salt Tolerance in Plants and Microorganisms: Toxicity Targets and Defense Responses", 1996, Int'l Review of Cytology 165:1-52.
Smirnoff N., "Plant resistance to environmental stress", 1998, Curr. Opin. Biotech. 9:214-219.

(Continued)

*Primary Examiner*—David H Kruse
(74) *Attorney, Agent, or Firm*—Elaine Sale; Mark Westhafer; Ruoying Chen

(57) ABSTRACT

A transgenic plant transformed by a potassium channel stress-related protein (PCSRP) coding nucleic acid, wherein expression of the nucleic acid sequence in the plant results in increased tolerance to environmental stress as compared to a wild type variety of the plant. Also provided are agricultural products, including seeds, produced by the transgenic plants. Also provided are isolated PCSRP, and isolated nucleic acid coding PCSRP, and vectors and host cells containing the latter. Further provided are methods of producing transgenic plants expressing PCSRP, methods of identifying novel PCSRP using antibodies, and methods of modifying the expression of PCSRP in plants.

29 Claims, 7 Drawing Sheets

OTHER PUBLICATIONS

Terry, N. and Ulrich, A., "Effects of Potassium Deficiency on the Photosynthesis and Respiration of Leaves of Sugar Beet", 1973, Plant Physiol. 51:783-786.

Zhu, J.-K. et al., "Genetic Analysis of Salt Tolerance in Arabidopsis: Evidence for a Critical Role of Potassium Nutrition", 1998, The Plant Cell 10:1181-91.

* cited by examiner

FIGURE 1

Nucleotide sequence of the partial AKT-1 from *Physcomitrella patens* (SEQ ID NO:1)

GCACGAGCAGATGAAGGCTGAGTCACTTCGGAAGTGCAGTGATCGTCTCTGTTTCTG
AGGAATATTTATCGTACAGTGCTCGTTTTGTTGAACTCGTCTTTATGTCTTGGTCGCG
AAGCCTTCCGTGACGCGGATTTGATAGCAGTTTTGCAGCTCACTGGGTAGGAGCGTT
CTTCACGCTCATGGTTTCAGTTTGGATGTTGTCGCTGGCTTTAGATTGCCTTTGGACG
ATGACTCAATTCGGTGAAAATTCGATAAGTTGCGTTTCGTAGTGAGCAGTCTCCCAG
AGGAATCTGCCATTGTGTAGCGAGGTGTAGGATCATGGGGTGGTCGGTAAGCGGGT
TGACCCACAAGGTCCTTGGAGCAGTGGGGCTGATGAAGTACGGCAATCAGCGCAAG
GCCTCTACCCCCAGCATCTTCAGCCATGCATACAGCAGCGGAATGTTGCCGGCTCTT
GGATCCAACCAGAGTACGAAGAACGTCCTTCAAAAGAAATACGTTATTCATCCTTAC
AACAAGAATTACAGGTACTGGCAGGGGATTTTGGTGGTGCTAGTGTTTTACTCCGCA
TGGGTGTCACCTTTCGAGTTTGGGTTCGTGCAAAATCCTCGCGGTGCTCTGTTAACTG
TCGACAATATTGTCAACTTTCTCTTCTTCATCGACATCGTATTGACCTTCTTCGTCGC
GTATCTCGACA

Nucleotide sequence of the full-length AKT-1 from *Physcomitrella patens* (SEQ ID NO:2)

GAATTCGCCCTTATCCCGGGCGTTTCGTAGTGAGCAGTCTCCCAGAGGAATCTGCCA

TTGTGTAGCGAGGTGTAGGATCATGGGGTGGTCGGTAAGCGGGTTGACCCACAAGG

TCCTTGGAGCAGTGGGGCTGATGAAGTACGGCAATCAGCGCAAGGCCTCTACCCCC

AGCATCTTCAGCCATGCATACAGCAGCGGAATGTTGCCGGCTCTTGGATCCAACCAG

AGTACGAAGAACGTCCTTCAAAAGAAATACGTTATTCATCCTTACAACAAGAATTAC

AGGTACTGGCAGGGGATTTTGGTGGTGCTAGTGTTTTACTCCGCATGGGTGTCACCT

TTCGAGTTTGGGTTCGTGCAAAATCCTCGCGGTGCTCTGTTAACTGTCGACAATATTG

TCAACTTTCTCTTCTTCATCGACATCGTATTGACCTTCTTCGTCGCGTATCTCGACAC

CTCAACTTTTTTGATGGAAGACAACTTGAAGAAGATCGCCATCAGGTATTTGAGAAC

ATGGTTTATTTTGGATGTTGTGTCGACTGTTCCATTGGCCGCAGTAATAGCGATTTTC

ACTGGAAAATATGAGACAGGGTTTGCGGCCAGTTTTGTCAATTTGTTGCGCCTCTGG

CGATTGCGCCGTGTGAGTGACGTGTTTGCGAGGGTGGAGAAGAATGTGAAATTTAG

TTACTTCTGGACTCGATGCCTCAAACTCTTTCTGGTGACTGTGTTTGTTTGCCACTTT

GCGGCCTGCTCGTACTACTTATTGGCTGCTCGACATCCGGCAAGCAAAGAGGCAGAT

ACGTGGCTAGGAGCTGTGCTCCCAAATTTTAAAGAGGAGTCACTGTGGGCGCGGTA

CGTGACGAGTATGTACTGGTCCATCACTACACTGGCGACTGTGGGATATGGCGATTT

GCATCCAGTCAACCGTGGTGAAATGATCTTCACCATCCTTTACATGTTGCTGAATCT

GGCATTGACTGCGTACATCATAGGAAACATGACCAATCTCATCACTCGTCTTACCGC

ACGAACTCGTGACTATCGTGACTCGGTGCAACAATTGGTGGAGTTTGCAACTAGAAA

TCAGTTGCCACGCAAGCTTCACGAGCAAATGATCTCCCACGTGCAGCTCAAGTTCAA

GACAGAGAGCCTTCAGCATCAAGGGACCATAGCCACCCTACCAAAGGCTATCCGCT

CATCTGTTGCGCAATTTCTGTTTTTTAACACAGTCGAGAAAGTGTACCTTTTCCAAGG

CACTTCTTACAATTTTCGTACTCAGCTGGTGTCGGAGATGAAGGTCGAGTTCTTCCCT

FIGURE 2

CCTCGCGAGGAAATTATTCTGGTTAACGAGGCCCCCTCCGAGTTTTACATAGTTGTG

AATGGTTCCGCGGATGTAATAATTCGAAGGGAGGAAGCCGGATCAGAGCAAATTCT

AATGACGGCTCAGGCAACTGATGTAATTGGCGAGATAGGGGTGATTTGTTACAGGC

CACAGCCTTTCACTGTGCGAAGTCGAAAGTTATCCCAGCTCTTGCGACTTGACCGCA

TTGTGTTTATGAACATTGTGCAACAATACAAGGAAGACGGCCAGAAGATTGTTGAC

AATCTGTTGCAGCGCTTGCGAGAAGCCTATGATCCTCGATTTGAGGAGCTTTCCTCT

GAGATTGAAGCCCTCCTTGTTGAAGGCGGCGAAATATCGGAACCAAGCGTATGTGC

GGTTGCTGCCGGAGGAAATGTGGAGGTTATGCAGCAGCTGTTGAGCAAAGGCGCGG

AGGTGGACAAGACAGATTATCACGGTCGGACTGCTCTGGTCATTGCATCATCAAAA

GGTTACGAGGAGTGCGTCAAGCTCCTTCTGGAACACGGAGCTGACCCCAACAAGGC

TGATGTGTATGGGAAGGTTCCTCTACTTGAGGCCCTTATTGCCCGCGACACGGCTAC

CGTGAAGCTCTTATCAGAGAACGGGGCGACCTTGAAAAATGCGGACATGGGGGTAT

ACCTCGGGCAAGCTGTGCTCGACTGTAATCGAGACCTCATTGACGACTACTTAAAAT

ATGGAACCGACATAAACACAGCAGGCGAATCTGAAGGACTGAGTGCGCTCCACATT

GCTGTTATTGATGGCAACATGGATATGGTGAGGTTTTTAGTATCCCGAGGAGCCGAC

CCTCACATCAAGCCTGGTGATGAGGCCACCCTTACCGCATACGAGCTAGCTGAGAG

AAGTGCAGATCACCCCGAAATAGCTTCCTTTTGAAGGCCCAATCAGTCCGCGATGA

ACCATACAGTTCCATCACGCCTAGAGAGTCGACATCTAACGCAAATCAGAAGAGGC

TTCCAAGGAAGGGAAGCTCCAATGTTGAATTCCAGATTGATGAGGTAACACCCCCG

CCTAGTCCAAATAAAGGATTTTCCGGAGAGCGAACGATACACTCATTAATGCGAAA

GCAGTCGGCTCGGGGCCGTCTCATGACTATAAGAGGACAGAAAACCCTCAGCCGGC

AACTAAACGCAAACCAGAACCCTTCAGGTTGGGGCTTGAGACGGCGTGACAATCGA

GACCCTCTTCAGACTTTTCCATCAGCTGGCGCTGCTAAGGAGGTTCCTCTTCGTGTCA

TCATCCATTCTTATCATCCTTGGAACAAGGAAGCGGTGGGACTTGGAAAGGTCGTTT

FIGURE 2 CONTINUED

TGCTGCCGAAAACTATTGAAGAGGTTCTCAAGATTGCGAACGAGAAATTCAACAAT

CATCCAACGAAGGTGTTGAACAAAGAGGCAGCTGAGATTGACGACTTGAGTGTCAT

CCGAGAAAACGACAACTTGTATGTCATTAACGATTCAGAGAAGTTGAACACGAGTT

CCCCCCCAGGGATGGACACAGATGACCTCATAGCAAGATTGCAAGCAATAGTCACA

GCATTGTCTCAACCCAAACCATAGACTCATGCATGCGACCAAGGTTGGGTATGTACT

TCTCATAAGCTTAGGACTCGACTTAGGATATCACGAGATCAGCGACAGTGTCTGAGC

TCGCAAGGGCGAATTC

FIGURE 2 CONTINUED

Deduced amino acid sequence of AKT-1 (SEQ ID NO.3)

MGWSVSGLTHKVLGAVGLMKYGNQRKASTPSIFSHAYSSGMLPALGSNQSTKNVLQK

KYVIHPYNKNYRYWQGILVVLVFYSAWVSPFEFGFVQNPRGALLTVDNIVNFLFFIDIVL

TFFVAYLDTSTFLMEDNLKKIAIRYLRTWFILDVVSTVPLAAVIAIFTGKYETGFAASFVN

LLRLWRLRRVSDVFARVEKNVKFSYFWTRCLKLFLVTVFVCHFAACSYYLLAARHPAS

KEADTWLGAVLPNFKEESLWARYVTSMYWSITTLATVGYGDLHPVNRGEMIFTILYML

LNLALTAYIIGNMTNLITRLTARTRDYRDSVQQLVEFATRNQLPRKLHEQMISHVQLKF

KTESLQHQGTIATLPKAIRSSVAQFLFFNTVEKVYLFQGTSYNFRTQLVSEMKVEFFPPR

EEIILVNEAPSEFYIVVNGSADVIIRREEAGSEQILMTAQATDVIGEIGVICYRPQPFTVRSR

KLSQLLRLDRIVFMNIVQQYKEDGQKIVDNLLQRLREAYDPRFEELSSEIEALLVEGGEIS

EPSVCAVAAGGNVEVMQQLLSKGAEVDKTDYHGRTALVIASSKGYEECVKLLLEHGA

DPNKADVYGKVPLLEALIARDTATVKLLSENGATLKNADMGVYLGQAVLDCNRDLID

DYLKYGTDINTAGESEGLSALHIAVIDGNMDMVRFLVSRGADPHIKPGDEATLTAYELA

ERSADHPEIASFLKAQSVRDEPYSSITPRESTSNANQKRLPRKGSSNVEFQIDEVTPPPSPN

KGFSGERTIHSLMRKQSARGRLMTIRGQKTLSRQLNANQNPSGWGLRRRDNRDPLQTFP

SAGAAKEVPLRVIIHSYHPWNKEAVGLGKVVLLPKTIEEVLKIANEKFNNHPTKVLNKE

AAEIDDLSVIRENDNLYVINDSEKLNTSSPPGMDTDDLIARLQAIVTALSQPKP*

FIGURE 3

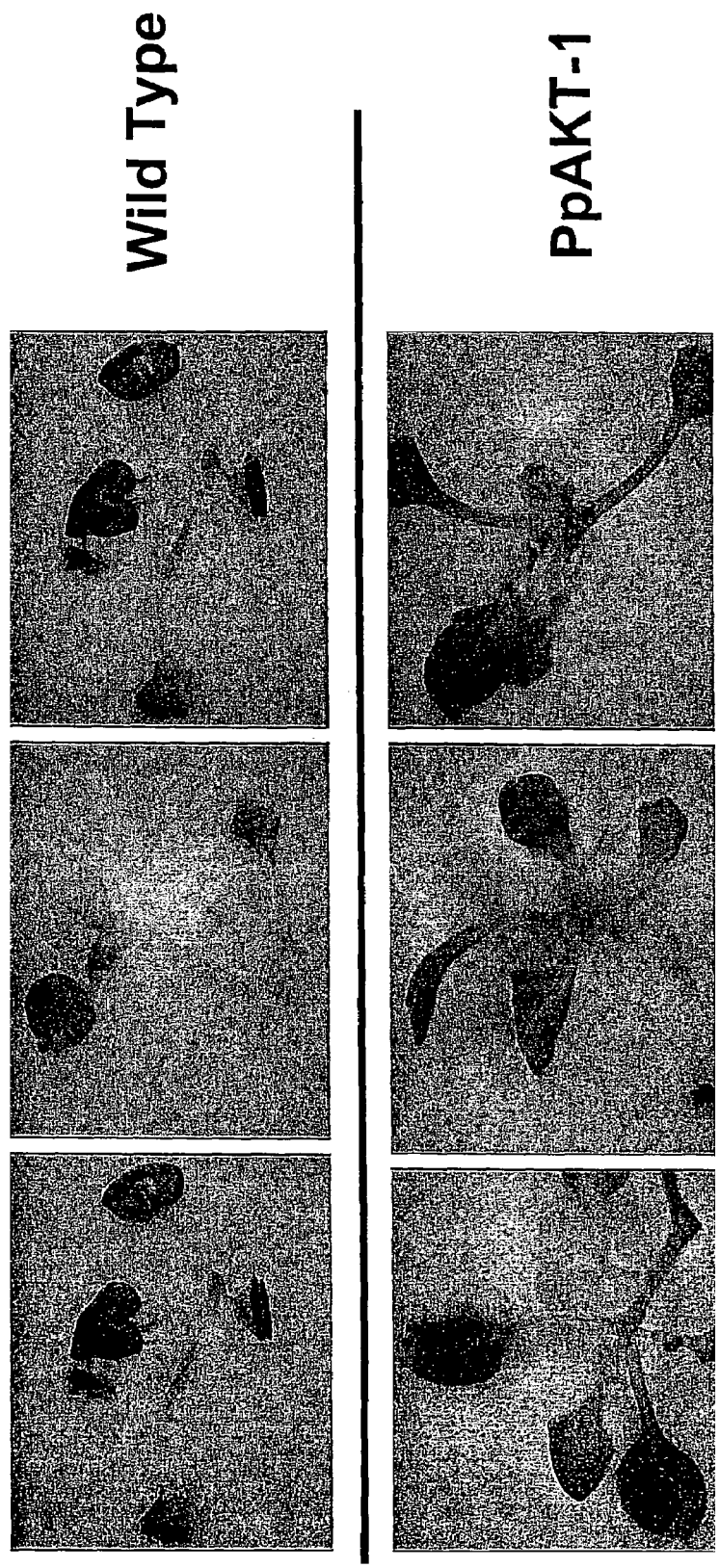

POTASSIUM CHANNEL STRESS-RELATED PROTEINS AND METHODS OF USE IN PLANTS

CROSS REFERENCE TO RELATED APPLICATIONS

This application is the National Stage of International Application No. PCT/US00/35356, filed Dec. 22, 2000, which claims priority to U.S. Provisional Application No. 60/171,745, filed Dec. 22, 1999.

BACKGROUND OF THE INVENTION

1. Field of the Invention

This invention relates generally to nucleic acid sequences encoding proteins that are associated with abiotic stress responses and abiotic stress tolerance in plants. In particular, this invention relates to nucleic acid sequences encoding proteins that confer drought, cold, and/or salt tolerance to plants.

2. Background Art

Environmental stress causes significant crop losses. The stresses are numerous and often crop- or location-specific. They include drought, high salinity, temperature extremes, hypoxia, mineral nutrient deficiency and UV-B radiation. Research in this area is driven by the hope of improving crop yield in afflicted areas. Currently, actual, but slow advances are being made by crop breeders and agronomists using tried- and tested-methodology. However, biotechnology will increasingly have a role as genes involved in stress tolerance are cloned and their mode of action elucidated (Quarrie S A, 1996 Plant Growth Reg. 20:167–178). By improving a plant's performance in response to different environmental stresses, the losses in productivity and risks to farming can be greatly reduced. Modifying a plant's tolerance to environmental stresses also allows a plant to be grown in regions where a plant or plant variety is typically unable to grow (Bohnert H. J and Jensen. R. G., 1996 TIBTECH 14:89–97). Many biochemical and physiological-basis for plant stress tolerance remain to be studied at the molecular level. However, it does appear that common damage from different stress (drought, salinity and cold stress) is mostly due to dehydration (Smirnoff N., 1998 Curre. Opi. Biotech. 9:214–219). The response that distinguishes drought (water stress)-tolerant and -sensitive plants more clearly is a dramatic accumulation of ions and solutes in tolerant species that leads to osmotic adjustments (Bohnert H. J and Jensen. R. G., 1996 TIBTECH 14:89–97). Drought and mineral nutrition may interact in a number of ways as a consequence of either (1) reduced transport of ions through the soil to the roots or (2) modified uptake of ions by roots. Potassium is particularly important in plants not only as a nutrient, but also as an osmoticum. Potassium may make a 30–50% contribution to water potential, particularly in older leaf tissue (Munns R. et al., 1979 Aust. J. Plant Physiol., 6:379–389). After prolonged drought in the field, potassium accumulates in leaves of ryegrass and barley, and could have a role in osmotic adjustment. In addition, potassium plays a key role in stomatal opening. A reduced supply of potassium therefore reduces stomatal conductance of $CO_2$ much more than it reduces internal conductance (Terry, N. and Ulrich, A., 1973 Plant Physiol. 51:783–786), because potassium is lost from the guard cells (Ehret, D. L. and Boyer, J. S. 1979 J. Experi. Bot. 30:225–234).

The fact that plant roots can absorb potassium over more than a 1000-fold concentration range and the concentration dependence of potassium uptake by a root has complex kinetics suggests the presence of multiple potassium uptake systems. Gene families encoding inward-rectifying potassium channels have been identified in several plant species. The AKT1 potassium channel gene is predominantly expressed in roots and genetic analysis indicates that it mediates the uptake of potassium in both the micromolar and millimolar ranges (Hirsch, R. H., et al., 1998 Science 280:918–921). Active transporters also participate in potassium uptake and several candidate genes encoding energized transporters have been identified (Hirsch. R. E and Sussman. M. R, 1999 TIBTECH. 17:356–361). In the past decade, study of potassium channels in plants has been focused on their function at the molecular level, yet none of the genes has been shown to improve stress tolerance in planta.

Due to the commercial consequences of environmental damage to crops, there is an interest in understanding how to improve a plant's response to environmental damage. By improving a plant's performance or survival in response to cold, drought and salinity, the environment stress-related risks of farming can be reduced. This invention fulfills this need by providing an improved method for modifying the response of a plant to environmental stresses, and in particular, provides nucleic acid and amino acid sequences of a novel potassium channel involved in plant stress responses.

SUMMARY OF THE INVENTION

The present invention provides a transgenic plant transformed by a potassium channel stress related protein (PCSRP) coding nucleic acid, wherein expression of the nucleic acid sequence in the plant results in increased tolerance to environmental stress as compared to a wild type variety of the plant. The invention provides that the PCSRP can be selected from one of the well known general classes of potassium channel proteins, including that known as active potassium transport protein (AKT). The invention further provides specific examples of PCSRP, and PCSRP coding nucleic acids, such as AKT-1.

The invention provides in some embodiments that the PCSRP and coding nucleic acid are that found in members of the genus *Physcomitrella*. In another preferred embodiment, the nucleic acid and protein are from a *Physcomitrella patens*. The invention provides that the environmental stress can be salinity, drought, temperature, metal, chemical, pathogenic and oxidative stresses, or combinations thereof. In preferred embodiments, the environmental stress can be drought.

The invention further provides a seed produced by a transgenic plant transformed by a PCSRP coding nucleic acid, wherein the plant is true breeding for increased tolerance to environmental stress as compared to a wild type variety of the plant. The invention further provides a seed produced by a transgenic plant expressing a PCSRP, wherein the plant is true breeding for increased tolerance to environmental stress as compared to a wild type variety of the plant.

The invention further provides an agricultural product produced by any of the above-described transgenic plants. The invention further provides an isolated PCSRP, wherein the PCSRP is as described below. The invention further provides an isolated PCSRP coding nucleic acid, wherein the PCSRP coding nucleic acid codes for a PCSRP as described below.

The invention further provides an isolated recombinant expression vector comprising a PCSRP coding nucleic acid as described below, wherein expression of the vector in a host cell results in increased tolerance to environmental stress as compared to a wild type variety of the host cell. The invention further provides a host cell containing the vector and a plant containing the host cell.

The invention further provides a method of producing a transgenic plant with a PCSRP coding nucleic acid, wherein expression of the nucleic acid in the plant results in increased tolerance to environmental stress as compared to a wild type variety of the plant comprising: (a) transforming a plant cell with an expression vector comprising a PCSRP coding nucleic acid, and (b) generating from the plant cell a transgenic plant with an increased tolerance to environmental stress as compared to a wild type variety of the plant. In preferred embodiments, the PCSRP is as described below. In preferred embodiments, the PCSRP coding nucleic acid is as described below.

The present invention further provides a method of identifying a novel PCSRP, comprising (a) raising a specific antibody response to a PCSRP, or fragment thereof, as described above; (b) screening putative PCSRP material with the antibody, wherein specific binding of the antibody to the material indicates the presence of a potentially novel PCSRP; and (c) analyzing the bound material in comparison to known PCSRP to determine its novelty. Alternatively, hybridization with nucleic acid probes as described above can be used to identify novel PCSRP nucleic acids.

The present invention also provides methods of modifying stress tolerance of a plant comprising, modifying the expression of a PCSRP in the plant, wherein the PCSRP is as described below. The invention provides that this method can be performed such that the stress tolerance is either increased or decreased.

BRIEF DESCRIPTION OF THE DRAWINGS

FIG. 1 shows a nucleotide sequence of a partial AKT-1 from *Physcomitrella patens* (SEQ ID NO:1)

FIG. 2 shows a nucleotide sequence of a full-length AKT-1 from *Physcomitrella patens* (SEQ ID NO:2).

FIG. 3 shows a deduced amino acid sequence of AKT-1 from *Physcomitrella patens* (SEQ ID NO:3).

FIG. 5 shows the results of a drought stress test with over-expressing PpAKT-1-transgenic plants and wild-type *Arabidopsis* lines. The transgenic lines display a tolerant phenotype. Individual transformant lines are shown.

DETAILED DESCRIPTION OF THE INVENTION

Figure 4:
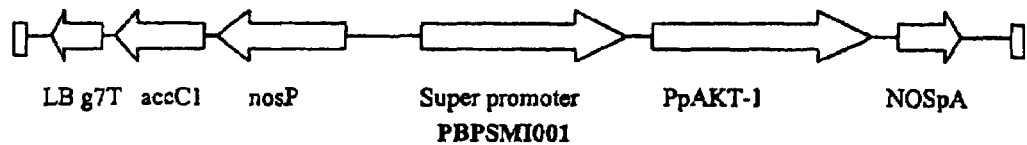
FIG. 4 shows a diagram of the plant expression vector pGMSG containing the super promoter driving the expression of the *Physcomitrella* potassium channel protein, AKT-1. The components are: aacCI gentamycin resistance gene (Hajdukiewicz et al., 1994 Plant Molecular Biology 25:989–94), NOS promoter (Becker et al., 1992 Plant Molecular Biology 20:1195–7), g7T terminator (Becker et al., 1992), NOSpA terminator (Jefferson et al., 1987 EMBO J. 6:3901–7). The plant expression vector, pBPSLVM001 contained the PpAKT-1 in the sense orientation under the constitutive super promoter.

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as "Potassium Channel Stress-related Proteins" (PCSRPs), in no way limits the functionality of those sequences.

The present invention provides a transgenic plant transformed by a PCSRP coding nucleic acid, wherein expression of the nucleic acid sequence in the plant results in increased tolerance to environmental stress as compared to a wild type variety of the plant. The invention further provides a seed produced by a transgenic plant transformed by a PCSRP coding nucleic acid, wherein the seed contains the PCSRP coding nucleic acid, and wherein the plant is true breeding for increased tolerance to environmental stress as compared to a wild type variety of the plant. The invention further provides a seed produced by a transgenic plant expressing a PCSRP, wherein the seed contains the PCSRP, and wherein the plant is true breeding for increased tolerance to environmental stress as compared to a wild type variety of the plant. The invention further provides an agricultural product produced by any of the above-or below-described transgenic plants. As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of a single DNA sequence introduced into a plant variety.

The invention further provides an isolated PCSRP. The invention provides that the PCSRP can be selected from one of the well known general classes of potassium channel proteins, including that known as active potassium transport protein (AKT). The invention further provides specific examples of PCSRP, and PCSRP coding nucleic acids, such as AKT-1. It is a novel finding of the present invention that these classes of potassium channels are involved in stress tolerance in plants and that expression of a member of one of these protein classes in a plant can increase that plant's tolerance to stress. The invention further provides specific examples of PCSRP, and PCSRP coding nucleic acids, such as AKT-1. In further preferred embodiments, the PCSRP is an active potassium transport protein-1 (AKT-1) as defined in SEQ ID NO:3, and homologues thereof. Homologues of amino acid sequences are defined below.

The invention further provides an isolated PCSRP coding nucleic acid. In preferred embodiments the PCSRP coding nucleic acid is an active potassium transport protein-1 (AKT-1) coding nucleic acid as defined in SEQ ID NO:2, and homologues thereof. Homologues of nucleotide sequences are defined below. The present invention includes PCSRP coding nucleic acids that encode PCSRPs as described herein. In some embodiments, the invention provides that the PCSRP is an active potassium transport protein-1 (AKT-1) as defined in SEQ ID NO:3. In one preferred embodiment, the nucleic acid and protein are isolated from the plant genus *Physcomitrella*. In another preferred embodiment, the nucleic acid and protein are from a *Physcomitrella patens* (*P. patens*) plant.

As used herein, the term "environmental stress" refers to any sub-optimal growing condition and includes, but is not limited to, sub-optimal conditions associated with salinity, drought, temperature, metal, chemical, pathogenic and oxidative stresses, or combinations thereof. In preferred embodiments, the environmental stress can be salinity, drought, and temperature, or combinations thereof, and in particular, can be high salinity, low water content and low temperature. In further preferred embodiments, the environmental stress can be drought. The invention provides a transgenic plant containing the PCSRP AKT-1 as defined herein, including homologues, wherein the environmental stress is drought. It is also to be understood that as used in the specification and in the claims, "a" or "an" can mean one or more, depending upon the context in which it is used. Thus, for example, reference to "a cell" can mean that at least one cell can be utilized.

In accordance with the purposes of this invention, as embodied and broadly described herein, this invention, in one aspect, provides an isolated nucleic acid from a moss encoding a Stress-related Protein (SRP), or a portion thereof. In particular, the present invention provides nucleic acids encoding PCSRPs including the nucleic acid sequence shown in SEQ ID NO:2. The present invention also provides amino acid sequences of PCSRPs including the amino acid sequence shown in SEQ ID NO:3. As mentioned above, the present invention describes for the first time the predicted *P. patens* active potassium transport protein (AKT-1). The present invention also describes for the first time that the *P. patens* active potassium transport protein (AKT-1) is useful for increasing stress tolerance in plants.

A nucleic acid molecule of the present invention, e.g., a nucleic acid molecule having the nucleotide sequence of SEQ ID NO:2, or a portion thereof, can be isolated using standard molecular biology techniques and the sequence information provided herein. For example, a *P. patens* PCSRP cDNA can be isolated from a *P. patens* library using all or portion of the sequence of SEQ ID NO:1 as a hybridization probe and standard hybridization techniques (e.g., as described in Sambrook et al., 1989 *Molecular Cloning: A Laboratory Manual.* 2nd, ed, Cold Spring Harbor Laboratory, Cold Spring Harbor Laboratory Press, Cold Spring Harbor, N.Y.). Moreover, a nucleic acid molecule encompassing all or a portion of the sequence of SEQ ID NO:1 can be isolated by the polymerase chain reaction using oligonucleotide primers designed based upon this sequence (e.g., a nucleic acid molecule encompassing all or a portion of the sequence of SEQ ID NO:1 can be isolated by the polymerase chain reaction using oligonucleotide primers designed based upon this same sequence of SEQ ID NO:1). For example, mRNA can be isolated from plant cells (e.g., by the guanidinium-thiocyanate extraction procedure of Chirgwin et al., 1979 Biochemistry 18:5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon the nucleotide sequence shown in SEQ ID NO:1. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a PCSRP nucleotide sequence can be prepared by standard synthetic techniques, e.g., using an automated DNA synthesizer.

In a preferred embodiment, an isolated nucleic acid molecule of the invention comprises the nucleotide sequence shown in SEQ ID NO:2. The sequence of SEQ ID NO:2 corresponds to the *Physcomitrella patens* PCSRP cDNA of the invention. This cDNA comprises sequences encoding PCSRPs (i.e., the "coding region", indicated in Table 1), as well as 5' untranslated sequences and 3' untranslated sequences. It is therefore to be understood that SEQ ID NO:2 comprises both coding region and 5' and 3' untranslated regions. Alternatively, the nucleic acid molecule can comprise only the coding region of the sequence in SEQ ID NO:2 or can contain whole genomic fragments isolated from genomic DNA. A coding region of these sequences is indicated as "ORF position".

In another preferred embodiment, an isolated nucleic acid molecule of the invention comprises a nucleic acid molecule which is a complement of the nucleotide sequence shown in SEQ ID NO:2, or a portion thereof. A nucleic acid molecule which is complementary to the nucleotide sequence shown in SEQ ID NO:2 is one which is sufficiently complementary to the nucleotide sequence shown in SEQ ID NO:2 such that it can hybridize to the nucleotide sequence shown in SEQ ID NO:2, thereby forming a stable duplex.

In still another preferred embodiment, an isolated nucleic acid molecule of the invention comprises a nucleotide sequence which is at least about 50–60%, preferably at least about 60–70%, more preferably at least about 70–80%, 80–90%, or 90–95%, and even more preferably at least about 95%, 96%, 97%, 98%, 99% or more homologous to a nucleotide sequence shown in SEQ ID NO:2, or a portion thereof. In an additional preferred embodiment, an isolated nucleic acid molecule of the invention comprises a nucleotide sequence which hybridizes, e.g., under stringent conditions, to the nucleotide sequence shown in SEQ ID NO:2, or a portion thereof. These hybridization conditions include washing with a solution having a salt concentration of about 0.02 molar at pH 7 at about 60° C.

Moreover, the nucleic acid molecule of the invention can comprise only a portion of the coding region of the sequence in SEQ ID NO:2, for example a fragment which can be used as a probe or primer or a fragment encoding a biologically active portion of a PCSRP. The nucleotide sequences determined from the cloning of the PCSRP genes from *P. patens* allows for the generation of probes and primers designed for use in identifying and/or cloning PCSRP homologues in other cell types and organisms, as well as PCSRP homologues from other mosses or related species. Therefore this invention also provides compounds comprising the nucleic acid molecules disclosed herein, or fragments thereof These compounds include the nucleic acid molecules attached to a moiety. These moieties include, but are not limited to, detection moieties, hybridization moieties, purification moieties, delivery moieties, reaction moieties, binding moieties, and the like. The probe/primer typically comprises substantially isolated oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of the sequence set forth in SEQ ID NO:2, an anti-sense sequence of the sequence set forth in SEQ ID NO:2, or naturally occurring mutants thereof. Primers based on a nucleotide sequence of SEQ ID NO:2 can be used in PCR reactions to clone PCSRP homologues. Probes based on the PCSRP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a PCSRP, such as by measuring a level of a PCSRP-encoding nucleic acid in a sample of cells, e.g., detecting PCSRP mRNA levels or determining whether a genomic PCSRP gene has been mutated or deleted.

In particular, a useful method to ascertain the level of transcription of the gene (an indicator of the amount of mRNA available for translation to the gene product) is to perform a Northern blot (for reference see, for example, Ausubel et al., 1988 Current Protocols in Molecular Biology, Wiley: New York), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information at least partially demonstrates the degree of transcription of the transformed gene. Total cellular RNA can be prepared from cells, tissues or organs by several methods, all well-known in the art, such as that described in Bormann, E. R. et al., 1992 Mol. Microbiol. 6:317–326.

To assess the presence or relative quantity of protein translated from this mRNA, standard techniques, such as a Western blot, may be employed (see, for example, Ausubel et al., 1988 Current Protocols in Molecular Biology, Wiley: New York). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or calorimetric label that may be readily detected. The presence and quantity of label observed indicates the presence and quantity of the desired mutant protein present in the cell.

In one embodiment, the nucleic acid molecule of the invention encodes a protein or portion thereof which includes an amino acid sequence which is sufficiently homologous to the amino acid sequence of SEQ ID NO:3 such that the protein or portion thereof maintains the same or a similar function as the amino acid sequence to which it is compared. As used herein, the language "sufficiently homologous" refers to proteins or portions thereof which have amino acid sequences which include a minimum number of identical or equivalent (e.g., an amino acid residue which has a similar side chain as an amino acid residue in one of the ORFs of the sequence of SEQ ID NO:3) amino acid residues to a PCSRP amino acid sequence such that the protein or portion thereof is able to participate in a stress tolerance response in a plant, or more particularly can act as a potassium channel involved in a stress tolerance response in a *Physcomitrella patens* plant. Examples of such activities are also described herein. Examples of PCSRP activities are set forth in Table 1.

In another embodiment, the protein is at least about 50–60%, preferably at least about 60–70%, and more preferably at least about 70–80%, 80–90%, 90–95%, and most preferably at least about 96%, 97%, 98%, 99% or more homologous to an entire amino acid sequence shown in SEQ ID NO:3. In yet another embodiment, at least about 50–60%, preferably at least about 60–70%, and more preferably at least about 70–80%, 80–90%, 90–95%, and most preferably at least about 96%, 97%, 98%, 99% or more homologous to an entire amino acid sequence encoded by the nucleic acid sequence shown in SEQ ID NO:2.

Portions of proteins encoded by the PCSRP nucleic acid molecules of the invention are preferably biologically active portions of one of the PCSRPs. As used herein, the term "biologically active portion of a PCSRP" is intended to include a portion, e.g., a domain/motif, of a PCSRP that participates in a stress tolerance response in a plant, or more particularly participates as a act as a potassium channel in a stress tolerance response in a plant, or has an activity as set forth in Table 1. To determine whether a PCSRP or a biologically active portion thereof can participate as a phosphatase in signal transduction pathways involved in a stress tolerance response in a plant, a stress analysis of a plant expressing the PCSRP may be performed. Such analysis methods are well known to those skilled in the art, as detailed in Example 7.

Additional nucleic acid fragments encoding biologically active portions of a PCSRP can be prepared by isolating a portion of the sequence in SEQ ID NO:3, expressing the encoded portion of the PCSRP or peptide (e.g., by recombinant expression in vitro) and assessing the activity of the encoded portion of the PCSRP or peptide.

The invention further encompasses nucleic acid molecules that differ from the nucleotide sequence shown in SEQ ID NO:2 (and portions thereof) due to degeneracy of the genetic code and thus encode the same PCSRP as that encoded by the nucleotide sequence shown in SEQ ID NO:2. In a further embodiment, the nucleic acid molecule of the invention encodes a full length *Physcomitrella patens* protein which is substantially homologous to an amino acid sequence of the polypeptide shown in SEQ ID NO:3.

In addition to the *Physcomitrella patens* PCSRP nucleotide sequence shown in SEQ ID NO:2, it will be appreciated by those skilled in the art that DNA sequence polymorphisms that lead to changes in the amino acid sequences of PCSRPs may exist within a population (e.g., the *Physcomitrella patens* population). Such genetic polymorphism in the PCSRP gene may exist among individuals within a population due to natural variation. As used herein, the terms "gene" and "recombinant gene" refer to nucleic acid molecules comprising an open reading frame encoding a PCSRP, preferably a *Physcomitrella patens* PCSRP. Such natural variations can typically result in 1–5% variance in the nucleotide sequence of the PCSRP gene. Any and all such nucleotide variations and resulting amino acid polymorphisms in a PCSRP that are the result of natural variation and that do not alter the functional activity of the PCSRPs are intended to be within the scope of the invention.

Nucleic acid molecules corresponding to natural variants and non- *Physcomitrella patens* homologues of the *Physcomitrella patens* PCSRP cDNA of the invention can be isolated based on their homology to *Physcomitrella patens* PCSRP nucleic acid disclosed herein using the *Physcomitrella patens* cDNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising the nucleotide sequence of SEQ ID NO:2. In other embbdiments, the nucleic acid is at least 30, 50, 100, 250 or more nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, 6.3.1–6.3.6, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:2 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *Physcomitrella patens* PCSRP.

In addition to naturally-occurring variants of the PCSRP sequence that may exist in the population, the skilled artisan will further appreciate that changes can be introduced by mutation into the nucleotide sequence of SEQ ID NO:2, thereby leading to changes in the amino acid sequence of the encoded PCSRP, without altering the functional ability of the PCSRP. For example, nucleotide substitutions leading to amino acid substitutions at "non-essential" amino acid residues can be made in the sequence of SEQ ID NO:2. A "non-essential" amino acid residue is a residue that can be altered from the wild-type sequence of the PCSRP (SEQ ID NO:3) without altering the activity of said PCSRP, whereas an "essential" amino acid residue is required for PCSRP activity. Other amino acid residues, however, (e.g., those that are not conserved or only semi-conserved in the domain having PCSRP activity) may not be essential for activity and thus are likely to be amenable to alteration without altering PCSRP activity.

Accordingly, another aspect of the invention pertains to nucleic acid molecules encoding PCSRPs that contain changes in amino acid residues that are not essential for PCSRP activity. Such PCSRPs differ in amino acid sequence from the sequence contained in SEQ ID NO:3, yet retain at least one of the PCSRP activities described herein. In one embodiment, the isolated nucleic acid molecule comprises a nucleotide sequence encoding a protein, wherein the protein comprises an amino acid sequence at least about 50% homologous to the amino acid sequence of SEQ ID NO:3 and is capable of participating in a stress tolerance response in a plant, or more particularly participates as a potassium channel in a stress tolerance response in a *Physcomitrella patens* plant, or has one or more activities set forth in Table 1. Preferably, the protein encoded by the nucleic acid molecule is at least about 50–60% homologous to the sequence of SEQ ID NO:3, more preferably at least about 60–70% homologous to the sequence of SEQ ID NO:3, even more preferably at least about 70–80%, 80–90%, 90–95% homologous to the sequence of SEQ ID NO:3, and most preferably at least about 96%, 97%, 98%, or 99% homologous to the sequence of SEQ ID NO:3.

To determine the percent homology of two amino acid sequences (e.g., the sequence of SEQ ID NO:3 and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., the sequence of SEQ ID NO:3) is occupied by the same amino acid residue or nucleotide at the corresponding position in the other sequence (e.g., a mutant form of the sequence selected from the polypeptide of SEQ ID NO:3), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=numbers of identical positions/total numbers of positions×100). Preferably, the length of sequence comparison is at least 15 amino acid residues, more preferably at least 25 amino acid residues, and most preferably at least 35 amino acid residues.

To determine the percent homology of two amino acid sequences (e.g., the sequence of SEQ ID NO:3 and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., the sequence of SEQ ID NO:3) is occupied by the same amino acid residue or nucleotide as the corresponding position in the other sequence (e.g., a mutant form of the sequence selected from the polypeptide of SEQ ID NO:3), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=numbers of identical positions/total numbers of positions×100). Preferably, the length of sequence comparison is at least 15 amino acid residues, more preferably at least 25 amino acid residues, and most preferably at least 35 amino acid residues.

Alternatively, a determination of the percent homology between two sequences can be accomplished using a mathematical algorithm. A preferred, non-limiting example of a mathematical algorithm utilized for the comparison of two sequences is the algorithm of Karlin and Altschul (1990 Proc. Natl. Acad. Sci. USA 90:5873–5877). Such an algorithm is incorporated into the NBLAST and XBLAST programs of Altschul, et al. (1990 J. Mol. Biol. 215:403–410). BLAST nucleic acid searches can be performed with the NBLAST program, score=100, wordlength=12 to obtain nucleic acid sequences homologous to PCSRP nucleic acid molecules of the invention. BLAST protein searches can be performed with the XBLAST program, score=50, wordlength=3 to obtain amino acid sequences homologous to PCSRPs of the present invention. To obtain gapped alignments for comparison purposes, Gapped BLAST can be utilized as described in Altschul et al. (1997 Nucleic Acids Res. 25:3389–3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used to obtain amino acid sequences homologous to the PCSRPs of the present invention. To obtain gapped alignments for comparison purposes, Gapped BLAST can be utilized as described in Altschul et al. (1997 Nucleic Acids Res. 25:3389–3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used.

An isolated nucleic acid molecule encoding a PCSRP homologous to the protein sequence of SEQ ID NO:3 can be created by introducing one or more nucleotide substitutions, additions or deletions into the nucleotide sequence of SEQ ID NO:2 such that one or more amino acid substitutions, additions or deletions are introduced into the encoded protein. Mutations can be introduced into the sequence of SEQ ID NO:2 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PCSRP is preferably replaced with another amino acid residue from the same side chain family. Alternatively, in another embodiment, mutations can be introduced randomly along all or part of a PCSRP coding sequence, such as by saturation mutagenesis, and the resultant mutants can be screened for a PCSRP activity described herein to identify mutants that retain PCSRP activity. Following mutagenesis of the sequence of SEQ ID NO:2, the encoded protein can be expressed recombinantly and the activity of the protein can be determined by analyzing the stress tolerance of a plant expressing the protein as described in Example 7.

In addition to the nucleic acid molecules encoding PCSRPs described above, another aspect of the invention pertains to isolated nucleic acid molecules that are antisense thereto. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PCSRP coding strand, or to only a portion thereof. In one embodiment, an antisense nucleic acid molecule is antisense to a "coding region" of the coding strand of a nucleotide sequence encoding a PCSRP. The term "coding region" refers to the region of the nucleotide sequence comprising codons which are translated into amino acid residues (e.g., the entire coding region of , , , , comprises nucleotides 1 to . . . ). In another embodiment, the antisense nucleic acid molecule is antisense to a "noncoding region" of the coding strand of a nucleotide sequence encoding PCSRP. The term "noncoding region" refers to 5' and 3' sequences that flank the coding region that are not translated into amino acids (i.e., also referred to as 5' and 3' untranslated regions).

Given the coding strand sequences encoding PCSRP disclosed herein (e.g., the sequence set forth in SEQ ID NO:2), antisense nucleic acids of the invention can be designed according to the rules of Watson and Crick base pairing. The antisense nucleic acid molecule can be complementary to the entire coding region of PCSRP mRNA, but more preferably is an oligonucleotide which is antisense to only a portion of the coding or noncoding region of PCSRP mRNA. For example, the antisense oligonucleotide can be complementary to the region surrounding the translation start site of PCSRP mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding a PCSRP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoters are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987 Nucleic Acids. Res. 15:6625–6641). The antisense nucleic acid molecule can also comprise a 2'-o-methylribonucleotide (Inoue et al., 1987 Nucleic Acids Res. 15:6131–6148) or a chimeric RNA-DNA analogue (Inoue et al., 1987 FEBS Lett. 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach, 1988 Nature 334:585–591)) can be used to catalytically cleave PCSRP mRNA transcripts to thereby inhibit translation of PCSRP mRNA. A ribozyme having specificity for a PCSRP-encoding nucleic acid can be designed based upon the nucleotide sequence of a PCSRP cDNA disclosed herein (i.e., SEQ ID NO:2) or on the basis of a heterologous sequence to be isolated according to methods taught in this invention. For example, a derivative of a *Tetrahymena* L-19 IVS RNA can be constructed in which the nucleotide sequence of the active site is complementary to the nucleotide sequence to be cleaved in an PCSRP-encoding mRNA. See, e.g., Cech et al. U.S. Pat. No. 4,987,071 and Cech et al. U.S. Pat. No. 5,116,742. Alternatively, PCSRP mRNA can be used to select a catalytic RNA having a specific ribonuclease activity from a pool of RNA molecules. See, e.g., Bartel, D. and Szostak, J. W., 1993 Science 261:1411–1418.

Alternatively, PCSRP gene expression can be inhibited by targeting nucleotide sequences complementary to the regulatory region of a PCSRP nucleotide sequence (e.g., a PCSRP promoter and/or enhancer) to form triple helical structures that prevent transcription of an PCSRP gene in target cells. See generally, Helene, C., 1991 Anticancer Drug Des. 6(6):569–84; Helene, C. et al., 1992 Ann. N.Y. Acad. Sci. 660:27–36; and Maher, L. J., 1992 Bioassays 14(12): 807–15.

The invention further provides an isolated recombinant expression vector comprising a nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990) or see: Gruber and Crosby, in: Methods in Plant Molecular Biology and Biotechnology, eds. Glick and Thompson, Chapter 7, 89–108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PCSRPs, mutant forms of PCSRPs, fusion proteins, etc.).

The recombinant expression vectors of the invention can be designed for expression of PCSRPs in prokaryotic or eukaryotic cells. For example, PCSRP genes can be expressed in bacterial cells such as *C. glutamicum*, insect cells (using baculovirus expression vectors), yeast and other fungal cells (see Romanos, M. A. et al., 1992 Foreign gene expression in yeast: a review, Yeast 8:423–488; van den Hondel, C. A. M. J. J. et al., 1991 Heterologous gene expression in filamentous fungi, in: More Gene Manipulations in Fungi, J. W. Bennet & L. L. Lasure, eds., p. 396–428: Academic Press: San Diego; and van den Hondel, C. A. M. J. J. & Punt, P. J., 1991 Gene transfer systems and vector development for filamentous fungi, in: Applied Molecular Genetics of Fungi, Peberdy, J. F. et al., eds., p. 1–28, Cambridge University Press: Cambridge), algae (Falciatore et al., 1999 Marine Biotechnology 1(3):239–251), ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella,* and *Stylonychia*, especially of the genus *Stylonychia lemnae* with vectors following a transformation method as described in WO 98/01572 and multicellular plant cells (see Schmidt, R. and Willmitzer, L., 1988 High efficiency *Agrobacterium tumefaciens*-mediated transformation of *Arabidopsis thaliana* leaf and cotyledon explants, Plant Cell Rep. 583–586); Plant Molecular Biology and Biotechnology, C Press, Boca Raton, Fla., chapter 6/7, S.71–119 (1993); F. F. White, B. Jenes et al., Techniques for Gene Transfer, in: Transgenic Plants, Vol. 1, Engineering and Utilization, eds. Kung und R. Wu, 128–43, Academic Press: 1993; Potrykus, 1991 Annu. Rev. Plant Physiol. Plant Molec. Biol. 42:205–225 and references cited therein) or mammalian cells. Suitable host cells are discussed further in Goeddel, *Gene Expression Technology: Methods in Enzymology* 185, Academic Press: San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S., 1988 Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the PCSRP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant PCSRP unfused to GST can be recovered by cleavage of the fusion protein with thrombin.

Examples of suitable inducible non-fusion *E. coli* expression vectors include pTrc (Amann et al., 1988 Gene 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in the bacterium chosen for expression, such as *C. glutamicum* (Wada et al., 1992 Nucleic Acids Res. 20:2111–2118). Such alteration of nucleic acid sequences of the invention can be carried out by standard DNA synthesis techniques.

In another embodiment, the PCSRP expression vector is a yeast expression vector. Examples of vectors for expression in yeast *S. cerevisiae* include pYepSec1 (Baldari, et al., 1987 Embo J. 6:229–234), pMFa (Kurjan and Herskowitz, 1982 Cell 30:933–943), pJRY88 (Schultz et al., 1987 Gene 54:113–123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) "Gene transfer systems and vector development for filamentous fungi, in: Applied Molecular Genetics of Fungi, J. F. Peberdy, et al., eds., p. 1–28, Cambridge University Press: Cambridge.

Alternatively, the PCSRPs of the invention can be expressed in insect cells using baculovirus expression vectors. Baculovirus vectors available for expression of proteins in cultured insect cells (e.g., Sf 9 cells) include the pAc series (Smith et al., 1983 Mol. Cell Biol. 3:2156–2165) and the pVL series (Lucklow and Summers, 1989 Virology 170:31–39).

In yet another embodiment, a nucleic acid of the invention is expressed in mammalian cells using a mammalian expression vector. Examples of mammalian expression vectors include pCDM8 (Seed, B., 1987 Nature 329:840) and pMT2PC (Kaufman et al., 1987 EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed.,* Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987 Genes Dev. 1:268–277), lymphoid-specific promoters (Calame and Eaton, 1988 Adv. Immunol. 43:235–275), in particular promoters of T cell receptors (Winoto and Baltimore, 1989 EMBO J. 8:729–733) and immunoglobulins (Banerji et al., 1983 Cell 33:729–740; Queen and Baltimore, 1983 Cell 33:741–748), neuron-specific promoters (e.g., the neurofilament promoter; Byrne and Ruddle, 1989 *PNAS* 86:5473–5477), pancreas-specific promoters (Edlund et al., 1985 Science 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990 Science 249:374–379) and the fetoprotein promoter (Campes and Tilghman, 1989 Genes Dev. 3:537–546).

In another embodiment, the PCSRPs of the invention may be expressed in unicellular plant cells (such as algae) (see Falciatore et al., 1999 Marine Biotechnology 1(3):239–251 and references therein) and plant cells from higher plants (e.g., the spermatophytes, such as crop plants). Examples of plant expression vectors include those detailed in: Becker, D., Kemper, E., Schell, J. and Masterson, R., 1992 New plant binary vectors with selectable markers located proximal to the left border, *Plant Mol. Biol.* 20: 1195–1197; and Bevan, M. W., 1984 Binary *Agrobacterium* vectors for plant transformation, Nucl. Acid. Res. 12:8711–8721; Vectors for Gene Transfer in Higher Plants; in: Transgenic Plants, Vol. 1, Engineering and Utilization, eds.: Kung and R. Wu, Academic Press, 1993, S. 15–38.

A plant expression cassette preferably contains regulatory sequences capable of driving gene expression in plants cells and which are operably linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984 EMBO J. 3:835) or functional equivalents thereof but also all other terminators functionally active in plants are suitable.

As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the protein per RNA ratio (Gallie et al., 1987 Nucl. Acids Research 15:8693–8711).

Plant gene expression has to be operably linked to an appropriate promoter conferring gene expression in a timely, cell or tissue specific manner. Preferred are promoters driving constitutive expression (Benfey et al., 1989 EMBO J. 8:2195–2202) like those derived from plant viruses like the 35S CAMV (Franck et al., 1980 Cell 21:285–294), the 19S CaMV (see also U.S. Pat. No. 5,352,605 and WO8402913) or plant promoters like those from Rubisco small subunit described in U.S. Pat. No. 4,962,028.

Other preferred sequences for use in plant gene expression cassettes are targeting-sequences necessary to direct the gene product in its appropriate cell compartment (for review see Kermode, 1996 Crit. Rev. Plant Sci. 15(4):285–423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells. Plant gene expression can also be facilitated via an inducible promoter (for review see Gatz, 1997 Annu. Rev. Plant Physiol. Plant Mol. Biol. 48:89–108). Chemically inducible promoters are especially suitable if gene expression is wanted to occur in a time specific manner. Examples of such promoters are a salicylic acid inducible promoter (WO 95/19443), a tetracycline inducible promoter (Gatz et al., 1992 Plant J. 2:397–404) and an ethanol inducible promoter (WO 93/21334).

Also, suitable promoters responding to biotic or abiotic stress conditions are those such as the pathogen inducible PRP1-gene promoter (Ward et al., 1993 Plant. Mol. Biol. 22:361–366), the heat inducible hsp80-promoter from tomato (U.S. Pat. No. 5,187,267), cold inducible alpha-amylase promoter from potato (WO 96/12814) or the wound-inducible pinII-promoter (EP 375091). For other examples of drought, cold, and salt-inducible promoters, such as the RD29A promoter, see Yamaguchi-Shinozalei et al. (1993 Mol. Gen. Genet. 236:331–340).

Especially those promoters are preferred which confer gene expression in specific tissues and organs, such as guard cells and the root hair cells. Suitable promoters include the napin-gene promoter from rapeseed (U.S. Pat. No. 5,608,152), the USP-promoter from Vicia faba (Baeumlein et al., 1991 Mol Gen Genet. 225(3):459–67), the oleosin-promoter from *Arabidopsis* (WO9845461), the phaseolin-promoter from *Phaseolus vulgaris* (U.S. Pat. No. 5,504,200), the Bce4-promoter from Brassica (WO9113980) or the legumin B4 promoter (LeB4; Baeumlein et al., 1992 Plant Journal, 2(2):233–9) as well as promoters conferring seed specific expression in monocot plants like maize, barley, wheat, rye, rice, etc. Suitable promoters to note are the lpt2 or lpt1-gene promoter from barley (WO 95/15389 and WO 95/23230) or those described in WO 99/16890 (promoters from the barley hordein-gene, rice glutelin gene, rice oryzin gene, rice prolamin gene, wheat gliadin gene, wheat glutelin gene, maize zein gene, oat glutelin gene, Sorghum kasirin-gene and rye secalin gene).

Also especially suited are promoters that confer plastid-specific gene expression as plastids are the compartment where precursors and some end products of lipid biosynthesis are synthesized. Suitable promoters are the viral RNA-polymerase promoter described in WO 95/16783 and WO 97/06250and the clpP-promoter from *Arabidopsis* described in WO 99/46394.

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to PCSRP mRNA. Regulatory sequences operatively linked to a nucleic acid molecule cloned in the antisense orientation can be chosen which direct the continuous expression of the antisense RNA molecule in a variety of cell types. For instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986 and Mol et al., 1990 FEBS Letters 268:427–430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a PCSRP can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms like *C. glutamicum*. Other suitable host cells are known to those skilled in the art.

Vector DNA can be introduced into prokaryotic or eukaryotic cells via conventional transformation or transfection techniques. As used herein, the terms "transformation", "transfection", "conjugation" and "transduction" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer and electroporation. Suitable methods for transforming or transfecting host cells including plant cells can be found in Sambrook, et al. (*Molecular Cloning: A Laboratory Manual.* 2nd, ed., *Cold Spring Harbor Laboratory, Cold Spring Harbor Laboratory Press, Cold Spring Harbor*, N.Y., 1989) and other laboratory manuals such as Methods in Molecular Biology, 1995, Vol. 44, *Agrobacterium* protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses and forage crops, these crops plants are also preferred target plants for a genetic engineering as one further embodiment of the present invention.

In particular, the invention provides a method of producing a transgenic plant with a PCSRP coding nucleic acid, wherein expression of the nucleic acid in the plant results in increased tolerance to environmental stress as compared to a wild type variety of the plant comprising: (a) transforming a plant cell with an expression vector comprising a PCSRP nucleic acid, and (b) generating from the plant cell a transgenic plant with a increased tolerance to environmental stress as compared to a wild type variety of the plant. In preferred embodiments, the PCSRP is as described above. In preferred embodiments, the PCSRP coding nucleic acid is as described above. The invention also provides a method of increasing expression of a gene of interest within a host cell as compared to a wild type variety of the host cell, wherein the gene of interest is transcribed in response to a PCSRP, comprising: (a) transforming the host cell with an expression vector comprising a PCSRP coding nucleic acid, and (b) expressing the PCSRP within the host cell, thereby increasing the expression of the gene transcribed in response to the PCSRP as compared to a wild type variety of the host cell. In preferred embodiments, the PCSRP is as described above. In preferred embodiments, the PCSRP coding nucleic acid is as described above.

For such plant transformation, binary vectors such as pBinAR can be used (Höfgen and Willmitzer, 1990 Plant Science 66:221–230). Construction of the binary vectors can be performed by ligation of the cDNA in sense or antisense orientation into the T-DNA. 5-prime to the cDNA a plant promoter activates transcription of the cDNA. A polyadenylation sequence is located 3-prime to the cDNA. Tissue-specific expression can be archived by using a tissue specific promoter. For example, seed-specific expression can be archived by-cloning the napin or LeB4 or USP promoter 5-prime to the cDNA. Also, any other seed specific promoter element can be used. For constitutive expression within the whole plant, the CaMV 35S promoter can be used. The expressed protein can be targeted to a cellular compartment using a signal peptide, for example for plastids, mitochondria or endoplasmic reticulum (Kermode, Crit. Rev. Plant Sci., 1996 4 (15):285–423). The signal peptide is cloned 5-prime in frame to the cDNA to archive subcellular localization of the fusion protein.

*Agrobacterium* mediated plant transformation can be performed using for example the GV3101(pMP90) (Koncz and Schell, 1986 Mol. Gen. Genet. 204:383–396) or LBA4404 (Clontech) *Agrobacterium tumefaciens* strain. Transformation can be performed by standard transformation techniques (Deblaere et al., 1994 Nucl. Acids. Res. 13:4777–4788). In one embodiment, promoters that are responsive to abiotic stresses can be used with, such as the *Arabidopsis* promoter RD29A, the nucleic acid sequences disclosed herein. One skilled in the art will recognize that the promoter used should be operatively linked to the nucleic acid such that the promoter causes transcription of the nucleic acid which results in the synthesis of an mRNA which encodes a polypeptide. Alternatively, the mRNA can be an antisense mRNA for use in affecting subsequent expression of the same or another gene or genes.

*Agrobacterium* mediated plant transformation can be performed using standard transformation and regeneration techniques (Gelvin, Stanton B. and Schilperoort, Robert A, Plant Molecular Biology Manual, 2nd Ed.—Dordrecht: Kluwer Academic Publ., 1995.—in Sect., Ringbuc Zentrale Signatur: BT11-P ISBN 0-7923-2731-4; Glick, Bernard R.; Thompson, John E., Methods in Plant Molecular Biology and Biotechnology, Boca Raton: CRC Press, 1993.—360 S.,ISBN 0-8493-5164-2). For example, rapeseed can be transformed via cotyledon or hypocotyl transformation (Moloney et al., 1989 Plant cell Report 8:238–242; De Block et al., 1989 Plant Physiol. 91:694–701). Use of antibiotica for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994 Plant Cell Report 13: 282–285. Additionally, transformation of soybean can be performed using for example a technique described in EP 0424 047, U.S. Pat. No. 5,322,783 (Pioneer Hi-Bred International) or in EP 0397 687, U.S. Pat. No. 5,376,543, U.S. Pat. No. 5,169,770 (University Toledo).

Plant transformation using particle bombardment, Polyethylene Glycol mediated DNA uptake or via the Silicon Carbide Fiber technique is for example described by Freeling and Walbot "The maize handbook" Springer Verlag: New York (1993) ISBN 3-540-97826-7. A specific example of maize transformation is found in U.S. Pat. No. 5,990,387 and a specific example of wheat transformation can be found in WO 93/07256.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate or in plants that confer resistance towards a herbicide such as glyphosate or glufosinate. Nucleic acid molecules encoding a selectable marker can be introduced into a host cell on the same vector as that encoding an PCSRP or can be introduced on a separate vector. Cells stably transfected with the introduced nucleic acid molecule can be identified by, for example, drug selection (e.g., cells that have incorporated the selectable marker gene will survive, while the other cells die).

To create a homologous recombinant microorganism, a vector is prepared which contains at least a portion of a PCSRP gene into which a deletion, addition or substitution has been introduced to thereby alter, e.g., functionally disrupt, the PCSRP gene. Preferably, this PCSRP gene is a *Physcomitrella patens* PCSRP gene, but it can be a homologue from a related plant or even from a mammalian, yeast, or insect source. In a preferred embodiment, the vector is designed such that, upon homologous recombination, the endogenous PCSRP gene is functionally disrupted (i.e., no longer encodes a functional protein; also referred to as a knock-out vector). Alternatively, the vector can be designed such that, upon homologous recombination, the endogenous PCSRP gene is mutated or otherwise altered but still encodes functional protein (e.g., the upstream regulatory region can be altered to thereby alter the expression of the endogenous PCSRP). To create a point mutation via homologous recombination, DNA-RNA hybrids can be used in a technique known as chimeraplasty (Cole-Strauss et al., 1999 Nucleic Acids Research 27(5):1323–1330 and Kmiec, 1999 Gene therapy American Scientist. 87(3):240–247). Homologous recombination procedures in *Physcomitrella patens* are also well known in the art and are contemplated for use herein.

Whereas in the homologous recombination vector, the altered portion of the PCSRP gene is flanked at its 5' and 3' ends by additional nucleic acid molecule of the PCSRP gene to allow for homologous recombination to occur between the exogenous PCSRP gene carried by the vector and an endogenous PCSRP gene in a microorganism or plant. The additional flanking PCSRP nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987 Cell 51:503 for a description of homologous recombination vectors or Strepp et al., 1998 PNAS, 95 (8):4368–4373 for cDNA based recombination in *Physcomitrella patens*). The vector is introduced into a microorganism or plant cell (e.g., via polyethylene glycol mediated DNA) and cells in which the introduced PCSRP gene has homologously recombined with the endogenous PCSRP gene are selected, using art-known techniques.

In another embodiment, recombinant microorganisms can be produced which contain selected systems which allow for regulated expression of the introduced gene. For example, inclusion of a PCSRP gene on a vector placing it under control of the lac operon permits expression of the PCSRP gene only in the presence: of IPTG. Such regulatory systems are well known in the art.

A host cell of the invention, such as a prokaryotic or eukaryotic host cell in culture, can be used to produce (i.e., express) a PCSRP. An alternate method can be applied in addition in plants by the direct transfer of DNA into developing flowers via electroporation or *Agrobacterium* medium gene transfer. Accordingly, the invention further provides methods for producing PCSRPs using the host cells of the invention. In one embodiment, the method comprises culturing the host cell of invention (into which a recombinant expression vector encoding a PCSRP has been introduced, or into which genome has been introduced a gene encoding a wild-type or altered PCSRP) in a suitable medium until PCSRP is produced. In another embodiment, the method further comprises isolating PCSRPs from the medium or the host cell.

Another aspect of the invention pertains to isolated PCSRPs, and biologically active portions thereof. An "isolated" or "purified" protein or biologically active portion thereof is free of some of the cellular material when produced by recombinant DNA techniques, or chemical precursors or other chemicals when chemically synthesized. The language "substantially free of cellular material" includes preparations of PCSRP in which the protein is separated from some of the cellular components of the cells in which it is naturally or recombinantly produced. In one embodiment, the language "substantially free of cellular material" includes preparations of PCSRP having less than about 30% (by dry weight) of non-PCSRP (also referred to herein as a "contaminating protein"), more preferably less than about 20% of non-PCSRP, still more preferably less than about 10% of non-PCSRP, and most preferably less than about 5% non-PCSRP. When the PCSRP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of PCSRP in which the protein is separated from chemical precursors or other chemicals that are involved in the synthesis of the protein. In one embodiment, the language "substantially free of chemical precursors or other chemicals" includes preparations of PCSRP having less than about 30% (by dry weight) of chemical precursors or non-PCSRP chemicals, more preferably less than about 20% chemical precursors or non-PCSRP chemicals, still more preferably less than about 10% chemical precursors or non-PCSRP chemicals, and most preferably less than about 5% chemical precursors or non-PCSRP chemicals. In preferred embodiments, isolated proteins or biologically active portions thereof lack contaminating proteins from the same organism from which the PCSRP is derived. Typically, such proteins are produced by recombinant expression of, for example, a *Physcomitrella patens* PCSRP in plants other than *Physcomitrella patens* or microorganisms such as *C. glutamicum*, ciliates, algae or fungi.

An isolated PCSRP or a portion thereof of the invention can participate in a stress tolerance response in a plant, or more particularly can participate as a potassium channel in a stress tolerance response in a *Physcomitrella patens* plant, or has one or more of the activities set forth in Table 1. In preferred embodiments, the protein or portion thereof comprises an amino acid sequence which is sufficiently homologous to an amino acid sequence encoded by the nucleic acid of SEQ ID NO:2 such that the protein or portion thereof maintains the ability to participate in the metabolism of compounds necessary for the construction of cellular membranes in *Physcomitrella patens*, or in the transport of molecules across these membranes. The portion of the protein is preferably a biologically active portion as described herein. In another preferred embodiment, a PCSRP of the invention has the amino acid sequence of SEQ ID NO:3. In yet another preferred embodiment, the PCSRP has an amino acid sequence which is encoded by a nucleotide sequence which hybridizes, e.g., under stringent conditions, to the nucleotide sequence of SEQ ID NO:2. In still another preferred embodiment, the PCSRP has an amino acid sequence which is at least about 50–60%, preferably at least about 60–70%, more preferably at least about 70–80%, 80–90%, 90–95%, and even more preferably at least about 96%, 97%, 98%, 99% or more homologous to the amino acid sequence of SEQ ID NO:3. The preferred PCSRPs of the present invention also preferably possess at least one of the PCSRP activities described herein. For example, a preferred PCSRP of the present invention includes an amino acid sequence encoded by a nucleotide sequence which hybridizes, e.g., under stringent conditions, to the nucleotide sequence of SEQ ID NO:2, and which can participate in a stress tolerance response in a plant, or more particularly can participate as a potassium channel involved in a stress tolerance response in a *Physcomitrella patens* plant, or which has one or more of the activities set forth in Table 1.

In other embodiments, the PCSRP is substantially homologous to the amino acid sequence of SEQ ID NO:3 and retains the functional activity of the protein of SEQ ID NO:3, yet differs in amino acid sequence due to natural variation or mutagenesis, as described in detail above. Accordingly, in another embodiment, the PCSRP is a protein which comprises an amino acid sequence which is at least about 50–60%, preferably at least about 60–70%, and more preferably at least about 70–80, 80–90, 90–95%, and most preferably at least about 96%, 97%, 98%, 99% or more homologous to the entire amino acid sequence of SEQ ID NO:3 and which has at least one of the PCSRP activities described herein. In another embodiment, the invention pertains to a full *Physcomitrella patens* protein which is substantially homologous to the entire amino acid sequence encoded by the nucleic acid of SEQ ID NO:2.

Biologically active portions of a PCSRP include peptides comprising amino acid sequences derived from the amino acid sequence of a PCSRP, e.g., the amino acid sequence of SEQ ID NO:3 or the amino acid sequence of a protein homologous to a PCSRP, which include fewer amino acids than a full length PCSRP or the full length protein which is homologous to a PCSRP, and exhibit at least one activity of a PCSRP. Typically, biologically active portions (peptides, e.g., peptides which are, for example, 5, 10, 15, 20, 30, 35, 36, 37, 38, 39, 40, 50, 100 or more amino acids in length) comprise a domain or motif with at least one activity of a PCSRP. Moreover, other biologically active portions, in which other regions of the protein are deleted, can be prepared by recombinant techniques and evaluated for one or more of the activities described herein. Preferably, the biologically active portions of a PCSRP include one or more selected domains/motifs or portions thereof having biological activity.

PCSRPs are preferably produced by recombinant DNA techniques. For example, a nucleic acid molecule encoding the protein is cloned into an expression vector (as described above), the expression vector is introduced into a host cell (as described above) and the PCSRP is expressed in the host cell. The PCSRP can then be isolated from the cells by an appropriate purification scheme using standard protein purification techniques. Alternative to recombinant expression, a PCSRP, polypeptide, or peptide can be synthesized chemically using standard peptide synthesis techniques. Moreover, native PCSRP can be isolated from cells (e.g., *Physcomitrella patens*), for example using an anti-PCSRP antibody, which can be produced by standard techniques utilizing a PCSRP or fragment thereof of this invention.

The invention also provides PCSRP chimeric or fusion proteins. As used herein, a PCSRP "chimeric protein" or "fusion protein" comprises a PCSRP polypeptide operatively linked to a non-PCSRP polypeptide. A "PCSRP polypeptide" refers to a polypeptide having an amino acid sequence corresponding to a PCSRP, whereas a "non-PC-SRP polypeptide" refers to a polypeptide having an amino acid sequence corresponding to a protein which is not substantially homologous to the PCSRP, e.g., a protein which is different from the PCSRP and which is derived from the same or a different organism. Within the fusion protein, the term "operatively linked" is intended to indicate that the PCSRP polypeptide and the non-PCSRP polypeptide are fused to each other so that both sequences fulfill the proposed function attributed to the sequence used. The non-PCSRP polypeptide can be fused to the N-terminus or C-terminus of the PCSRP polypeptide. For example, in one embodiment, the fusion protein is a GST-PCSRP fusion protein in which the PCSRP sequences are fused to the C-terminus of the GST sequences. Such fusion proteins can facilitate the purification of recombinant PCSRPs. In another embodiment, the fusion protein is a PCSRP containing a heterologous signal sequence at its N-terminus. In certain host cells (e.g., mammalian host cells), expression and/or secretion of a PCSRP can be increased through use of a heterologous signal sequence.

Preferably, a PCSRP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, *Current Protocols in Molecular Biology*, Eds. Ausubel et al. John Wiley & Sons: 1992). Moreover, many expression vectors are commercially available that already encode a fusion moiety (e.g., a GST polypeptide). A PCSRP-encoding nucleic acid can be cloned into such an expression vector such that the fusion moiety is linked in-frame to the PCSRP.

Homologues of the PCSRP can be generated by mutagenesis, e.g., discrete point mutation or truncation of the PCSRP. As used herein, the term "homologue" refers to a variant form of the PCSRP which acts as an agonist or antagonist of the activity of the PCSRP. An agonist of the PCSRP can retain substantially the same, or a subset, of the biological activities of the PCSRP. An antagonist of the PCSRP can inhibit one or more of the activities of the naturally occurring form of the PCSRP, by, for example, competitively binding to a downstream or upstream member of the cell membrane component metabolic cascade which includes the PCSRP, or by binding to a PCSRP which mediates transport of compounds across such membranes, thereby preventing translocation from taking place.

In an alternative embodiment, homologues of the PCSRP can be identified by screening combinatorial libraries of mutants, e.g., truncation mutants, of the PCSRP for PCSRP agonist or antagonist activity. In one embodiment, a variegated library of PCSRP variants is generated by combinatorial mutagenesis at the nucleic acid level and is encoded by a variegated gene library. A variegated library of PCSRP variants can be produced by, for example, enzymatically ligating a mixture of synthetic oligonucleotides into gene sequences such that a degenerate set of potential PCSRP sequences is expressible as individual polypeptides, or alternatively, as a set of larger fusion proteins (e.g., for phage display) containing the set of PCSRP sequences therein. There are a variety of methods which can be used to produce libraries of potential PCSRP homologues from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential PCSRP sequences. Methods for synthesizing degenerate oligonucleotides are known in the art (see, e.g., Narang, S. A., 1983 Tetrahedron 39:3; Itakura et al., 1984 Annu. Rev. Biochem. 53:323; Itakura et al., 1984 Science 198:1056; Ike et al., 1983 Nucleic Acid Res. 11:477).

In addition, libraries of fragments of the PCSRP coding can be used to generate a variegated population of PCSRP fragments for screening and subsequent selection of homologues of a PCSRP. In one embodiment, a library of coding sequence fragments can be generated by treating a double stranded PCR fragment of a PCSRP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PCSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PCSRP homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify PCSRP homologues (Arkin and Yourvan, 1992 PNAS 89:7811–7815; Delgrave et al., 1993 Protein Engineering 6(3):327–331). In another embodiment, cell based assays can be exploited to analyze a variegated PCSRP library, using methods well known in the art. The present invention further provides a method of identifying a novel PCSRP, comprising (a) raising a specific antibody response to a PCSRP, or fragment thereof, as described above; (b) screening putative PCSRP material with the antibody, wherein specific binding of the antibody to the material indicates the presence of a potentially novel PCSRP; and (c) analyzing the bound material in comparison to known PCSRP to determine its novelty.

The nucleic acid molecules, proteins, protein homologues, fusion proteins, primers, vectors, and host cells described herein can be used in one or more of the following methods: identification of *Physcomitrella patens* and related organisms; mapping of genomes of organisms related to *Physcomftrella patens*; identification and localization of *Physcomitrella patens* sequences of interest; evolutionary studies; determination of PCSRP regions required for function; modulation of a PCSRP activity; modulation of the metabolism of ohe or more cell functions; modulation of the transmembrane transport of one or more compounds; and modulation of stress resistance.

The moss *Physcomitrella patens* represents one member of the mosses. It is related to other mosses such as *Ceratodon purpureus* which is capable of growth in the absence of light. Mosses like *Ceratodon* and *Physcomitrella* share a high degree of homology at the DNA sequence and polypeptide levels allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The PCSRP nucleic acid molecules of the invention have a variety of uses. Most importantly, the nucleic acid and amino acid sequences of the present invention can be used to transform plants, thereby inducing tolerance to stresses such as drought, high salinity and cold. The present invention therefore provides a transgenic plant transformed by a PCSRP coding nucleic acid, wherein expression of the nucleic acid sequence in the plant results in increased tolerance to environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass and forage crops, for example. In particular, the present invention describes using the expression of AKT-1 (SEQ ID NO:3) to engineer drought-tolerant plants. This strategy has herein been demonstrated for *Arabidopsis thaliana*, Rapeseed/Canola, soybeans, corn and wheat but its application is not restricted to these plants. Accordingly, the invention provides a transgenic plant containing a PCSRP, such as AKT-1 as defined above, including homologues, wherein the environmental stress is drought. This invention also describes the principle of using over-expression of AKT-1 (SEQ ID NO:3) to engineer salt-tolerant plants. Again, this strategy has herein been demonstrated for *Arabidopsis thaliana*, Rapeseed/Canola, soybeans, corn and wheat but its application is not restricted to these plants. Accordingly, the invention provides a transgenic plant containing the PCSRP such as AKT-1 as defined above, including homologues, wherein the environmental stress is salinity.

The present invention also provides methods of modifying stress tolerance of a plant comprising, modifying the expression of a PCSRP in the plant. The invention provides that this method can be performed such that the stress tolerance is either increased or decreased.

Furthermore, this method can be used wherein the plant is either transgenic or not transgenic. In cases when the plant is transgenic, the plant can be transformed with a vector containing any of the above described PCSRP coding nucleic acids, or the plant can be transformed with a promoter that directs expression of native PCSRP in the plant, for example. The invention provides that such a promoter can be tissue specific. Furthermore, such a promoter can be developmentally regulated. Alternatively, non-transgenic plants can have native PCSRP expression modified by inducing a native promoter. Furthermore, the invention provides that PCSRP expression can be modified by administration of an anti-sense molecule that inhibits expression of PCSRP.

The expression of AKT-1 (SEQ ID NO:3) in target plants can be accomplished by, but is not limited to, one of the following examples: (a) constitutive promoter, (b) stress-inducible promoter, (c) chemical-induced promoter, and (d) engineered promoter over-expression with for example zinc-finger derived transcription factors (Greisman and Pabo, 1997 Science 275:657). The later case involves identification of the AKT-1 (SEQ ID NO:3) homologues in the target plant as well as from its promoter. Zinc-finger-containing recombinant transcription factors are engineered to specifically interact with the AKT-1 (SEQ ID NO:3) homologue and transcription of the corresponding gene is activated.

As shown herein and described more fully below, expression of the PCSRP AKT-1 (SEQ ID NO:3) in *Arabidopsis thaliana* confers a high degree of drought tolerance to the plant. Additionally, AKT-1 (SEQ ID NO:3) confers tolerance to high salt concentrations to this plant.

In addition to introducing the PCSRP nucleic acid sequences into transgenic plants, these sequences can also be used to identify an organism as being *Physcomitrella patens* or a close relative thereof. Also, they may be used to identify the presence of *Physcomitrella patens* or a relative thereof in a mixed population of microorganisms. The invention provides the nucleic acid sequences of a number of *Physcomitrella patens* genes; by probing the extracted genomic DNA of a culture of a unique or mixed population of microorganisms under stringent conditions with a probe spanning a region of a *Physcomitrella patens* gene which is unique to this organism, one can ascertain whether this organism is present.

Further, the nucleic acid and protein molecules of the invention may serve as markers for specific regions of the genome. This has utility not only in the mapping of the genome, but also in functional studies of *Physcomitrella patens* proteins. For example, to identify the region of the genome to which a particular *Physcomitrella patens* DNA-binding protein binds, the *Physcomitrella patens* genome could be digested, and the fragments incubated with the DNA-binding protein. Those which bind the protein may be additionally probed with the nucleic acid molecules of the invention, preferably with readily detectable labels; binding of such a nucleic acid molecule to the genome fragment enables the localization of the fragment to the genome map of *Physcomitrella patens*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related mosses.

The PCSRP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

Manipulation of the PCSRP nucleic acid molecules of the invention may result in the production of PCSRPs having functional differences from the wild-type PCSRPs. These proteins may be improved in efficiency or activity, may be present in greater numbers in the cell than is usual, or may be decreased in efficiency or activity. There are a number of mechanisms by which the alteration of a PCSRP of the invention may directly affect stress response and/or stress tolerance. In the case of plants expressing PCSRPs, increased transport can lead to improved salt and/or solute partitioning within the plant tissue and organs. By either increasing the number or the activity of transporter molecules which export ionic molecules from the cell, it may be possible to affect the salt tolerance of the cell.

The effect of the genetic modification in plants, *C. glutamicum*, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, protein synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469–714, VCH: Weinheim; Belter, P. A. et al., 1988 Bioseparations: downstream processing for biotechnology, John Wiley and Sons; Kennedy, J. F. and Cabral, J. M. S., 1992 Recovery processes for biological materials, John Wiley and Sons; Shaeiwitz, J. A. and Henry, J. D., 1988 Biochemical separations, in: Ulmann's Encyclopedia of Industrial Chemistry, vol. B3, Chapter 11, page 1–27, VCH: Weinheim; and Dechow, F. J. (1989) Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their tolerance to drought, salt, and temperature stress. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatula*, etc., using standard protocols. The resulting transgenic cells and/or plants derived therefrom can then be assayed for fail or alteration of their tolerance to drought, salt, and temperature stress.

The engineering of one or more PCSRP genes of the invention may also result in PCSRPs having altered activities which indirectly impact the stress response and/or stress tolerance of algae, plants, ciliates or fungi or other microorganisms like *C. glutamicum*. For example, the normal biochemical processes of metabolism result in the production of a variety of products (e.g., hydrogen peroxide and other reactive oxygen species) which may actively interfere with these same metabolic processes (for example, peroxynitrite is known to nitrate tyrosine side chains, thereby inactivating some enzymes having tyrosine in the active site (Groves, J. T., 1999 Curr. Opin. Chem. Biol. 3(2):226–235).

While these products are typically excreted, cells can be genetically altered to transport more products than is typical for a wild-type cell. By optimizing the activity of one or more PCSRPs of the invention which are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells. (Girke, T., 1998 The Plant Journal 15:39–48). The resultant knockout cells can then be evaluated for their ability or capacity to tolerate various stress conditions, their response to various stress conditions, and the effect on the phenotype and/or genotype of the mutation. For other methods of gene inactivation include U.S. Pat. No. 6,004,804 "Non-Chimeric Mutational Vectors" and Puttaraju et al., 1999 Spliceosome-mediated RNA trans-splicing as a tool for gene therapy Nature Biotechnology 17:246–252.

The aforementioned mutagenesis strategies for PCSRPs to result in increased stress resistance are not meant to be limiting; variations on these strategies will be readily apparent to one skilled in the art. Using such strategies, and incorporating the mechanisms disclosed herein, the nucleic acid and protein molecules of the invention may be utilized to generate algae, ciliates, plants, fungi or other microorganisms like *C. glutamicum* expressing mutated PCSRP nucleic acid and protein molecules such that the stress tolerance is improved.

The present invention also provides antibodies which specifically bind to a PCSRP-polypeptide, or a portion thereof, as encoded by a nucleic acid disclosed herein or as described herein. Antibodies can be made by many well-known methods (See, e.g. *Harlow and Lane*, "Antibodies; A Laboratory Manual" Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992 Bio/Technology 10:163–167; Bebbington et al., 1992 Bio/Technology 10:169–175).

The phrases "selectively binds" and "specifically binds" with the polypeptide refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies selectively bind with a particular protein. For example, solid-phase ELISA immunoassays are routinely used to select antibodies selectively immunoreactive with a protein. See *Harlow and Lane* "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology,"0 (Lange Medical Publications, Los Altos, Calif., Fourth Edition) and references cited therein, and in Harlow and Lane ("Antibodies, A Laboratory Manual" Cold Spring Harbor Publications, New York, 1988).

Throughout this application various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. Additionally, all references cited herein are hereby expressly incorporated herein by reference.

EXAMPLES

Example 1

Growth of *Physcomitrella patens* Cultures

For this study, plants of the species *Physcomitrella patens* (Hedw.) B.S.G. from the collection of the genetic studies section of the University of Hamburg were used. They originate from the strain 16/14 collected by H. L. K. Whitehouse in Gransden Wood, Huntingdonshire (England), which was subcultured from a spore by Engel (1968, Am. J. Bot. 55, 438–446). Proliferation of the plants was carried out by means of spores and by means of regeneration of the gametophytes. The protonem a developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromol s$^{-1}$ m$^{-2}$ (white light; Philips TL 65W/25 fluorescent tube) and a light/dark change of 16/8 hours. The moss was either modified in liquid culture using Knop medium according to Reski and Abel (1985, Planta 165:354–358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation From Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylsarcosine buffer, 20 µl of β-mercaptoethanol and 10 µl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 min using ice-cold isopropanol. The precipitated DNA was sedimented at 4° C. and 10,000 g for 30 minutes and resuspended in 180 µl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 µl of $H_2O$+RNAse (50 mg/ml final concentration). The DNA was dissolved overnight at 4° C. and the RNAse digestion was subsequently carried out at 37° C. for 1 hour. Storage of the DNA took place at 4° C.

Example 3

Isolation of Total RNA and Poly-(A)+ RNA and cDNA Library Construction from *Physcomitrella patens*

For the investigation of transcripts, both total RNA and poly-(A)$^+$ RNA were isolated. The total RNA was obtained from wild-type 9 day old protonemata following the GTC-method (Reski et al. 1994, Mol. Gen. Genet., 244:352–359). The Poly(A)+ RNA was isolated using Dyna Beads$^R$ (Dynal, Oslo, Norway) following the instructions of the manufacturers protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour) and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown *E. coli* cultures grown in Luria-Broth medium containing ampicillin (see Sambrook et al. 1989 Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

| | |
|---|---|
| 5'-CAGGAAACAGCTATGACC-3' | SEQ ID NO:4 |
| 5'-CTAAAGGGAACAAAAGCTG-3' | SEQ ID NO:5 |
| 5'-TGTAAAACGACGGCCAGT-3' | SEQ ID NO:6 |

Sequences were processed and annotated using the software package EST-MAX commercially provided by BioMax (Munich, Germany). The program incorporates practically all bioinformatics methods important for functional and structural characterization of protein sequences. For reference the website at pedant.mips.biochem.mpg.de. The most important algorithms incorporated in EST-MAX are: FASTA: Very sensitive sequence database searches with estimates of statistical significance; Pearson W. R. (1990) Rapid and sensitive sequence comparison with FASTP and FASTA. Methods Enzymol. 183:63–98; BLAST: Very sensitive sequence database searches with estimates of statistical significance. Altschul S. F., Gish W., Miller W., Myers E. W., and Lipman D. J. Basic local alignment search tool. Journal of Molecular Biology 215:403–10; PREDATOR: High-accuracy secondary structure prediction from single and multiple sequences. Frishman, D. and Argos, P. (1997) 75% accuracy in protein secondary structure prediction. Proteins, 27:329–335; CLUSTALW: Multiple sequence alignment. Thompson, J. D., Higgins, D. G. and Gibson, T. J. (1994) CLUSTAL W: improving the sensitivity of progressive multiple sequence alignment through sequence weighting, positions-specific gap) penalties and weight matrix choice. Nucleic Acids Research, 22:4673–4680; TMAP: Transmembrane region prediction from multiply aligned sequences. Persson, B. and Argos, P. (1994) Prediction of transmembrane segments in proteins utilizing multiple sequence alignments. J. Mol. Biol. 237:182–192; ALOM2: Transmembrane region prediction from single sequences. Klein, P., Kanehisa, M., and DeLisi, C. Prediction of protein function from sequence properties: A discriminate analysis of a database. Biochim. Biophys. Acta 787:221–226 (1984). Version 2 by Dr. K. Nakai; PROSEARCH: Detection of PROSITE protein sequence patterns. Kolakowski L. F. Jr., Leunissen J. A. M., Smith J. E. (1992) ProSearch: fast searching of protein sequences with regular expression patterns related to protein structure and function. Biotechniques 13, 919–921; BLIMPS: Similarity searches against a database of ungapped blocks. J. C. Wallace and Henikoff S., (1992); PATMAT: A searching and extraction program for sequence, pattern and block queries and databases, CABIOS 8:249–254. Written by Bill Alford.

Example 5

Identification of *Physcomitrella patens* ORF Corresponding to PpAKT-1

The *Physcomitrella patens* partial cDNA (ESTs) shown in Table 1 below was identified in the *Physcomitrella patens* EST sequencing program using the program EST-MAX through BLAST analysis. The Sequence Identification Number corresponding to this EST is SEQ ID NO:1. The top hits of the BLAST analysis were potassium channel (Swiss-Prot accession numbers: 004242, Q38998 and Q9LEG6) ORFs. (Table 2)

TABLE 1

| Functional Category | Putative Function | Sequence Code | ORF position | Name |
|---|---|---|---|---|
| Ion Transport | potassium channel | c_pp001062070r | 258–695 | PpAKT-1 |

TABLE 2

Amino acid comparison of the PpAKT-1 and other homologous proteins (GCG Gap program was used: gap penalty: 10; gap extension penalty: 0.1; score matrix: blosum62)

| | Swiss.-Prot II | | | | |
|---|---|---|---|---|---|
| | Q04242 | Q24382 | Q38998 | Q9LEG6 | Q9LKP3 |
| Protein name | Potassium channel | Potassium channel | AKT1 potassium transporter | Potassium channel | Putative Potassium channel protein MKT1P |
| specie | Zea mays (Maize) | Solanum tuberosum (Potato) | Arabidopsis thaliana (Mouse-ear cress) | Lycopersicon esculentum (Tomato) | Mesembryanthemum crystallinum (Common ice plant) |
| Identity % | 41% | 40% | 41% | 41% | 40% |
| Similarity % | 55% | 56% | 55% | 56% | 56% |

Example 6

Cloning of the Full-Length *Physcomitrella patens* cDNA Encoding for PpAKT-1

As described below, a full-length sequence corresponding to the partial cDNA PpAKT-1 (SEQ ID NO:1) was obtained by performing polymerase chain reaction (PCR) with gene-specific EST as the template DNA. The percent peptide sequence identity between the PpAKT-1 and other polypeptides showed that the PpAKT-1 has sequence identity with other plant potassium channels with a range of 40–41% over most of the length of the sequences as shown in Table 2.

The synthetic oligonucleotide primers (MWG-Biotech) for the reaction were: 14F: 5'-ATCCCGGGCGTTTCG-TAGTGAGCAGTCTCCCA-3' (SEQ ID NO:7) and 14R: 5'-GCGAGCTCAGACACTGTCGCTGATCTCGTGAT-3' (SEQ ID NO:8). The primers designed contained a XmaI site in the 5' region and a SacI site in the 3' region for cloning purposes. The conditions for the reaction were standard conditions with PWO DNA polymerase (Roche). PCR was performed according to standard conditions and to manufacture's protocols (Sambrook et al. 1989, Biometra T3 Thermocycler). The parameters for the reaction were: five minutes at 94° C. followed by five cycles of one minute at 94° C., one minute at 50° C. and 4 minutes at 72° C. This was followed by twenty five cycles of one minute at 94° C., one minute at 65° C. and 4 minutes at 72° C. These parameters generated a fragment 4.0 kilobases long. The fragment was extracted from agarose gel with a QIAquick Gel Extraction Kit (Qiagen) and ligated into the TOPO pCR 2.1 vector (Invitrogen) following manufacture's instructions. Recombinant vectors were transformed into Top10 cells (Invitrogen) using standard conditions (Sambrook et al. 1989). Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside) grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacture's instructions. Analyses of subsequent clones and restriction mapping was performed according to standard molecular biology techniques (Sambrook et al. 1989).

Example 7

Engineering Stress-tolerant *Arabidopsis* Plants by Overexpressing the pPAKT-1 Gene Binary Vector Construction: pGMSG The pLMNC53 (Mankin, 2000, PhD thesis) vector was digested with HindIII (Roche) and blunt-end filled with Klenow enzyme and 0.1 mM dNTPs (Roche) according to manufacturer's instructions. This fragment was extracted from agarose gel with a QIAquick Gel Extraction Kit (Qiagen) according to manufacturer's instructions. The purified fragment was then digested with EcoRI (Roche) according to manufacturer's instructions. This fragment was extracted from agarose gel with a QIAquick Gel Extraction Kit (Qiagen) according to manufacturer's instructions. The resulting 1.4 kilobase fragment, the gentamycin cassette, included the nos promoter, aacCI gene and the g7 terminator.

The vector pBlueScript was digested with EcoRI and SmaI (Roche) according to manufacturer's instructions. The resulting fragment was extracted from agarose gel with a QIAquick Gel Extraction Kit (Qiagen) according to manufacturer's instructions. The digested pBlueScript vector and the gentamycin cassette fragments were ligated with T4 DNA Ligase (Roche) according to manufacturer's instructions, joining the two respective EcoRI sites and joining the blunt-ended HindIII site with the SmaI site.

The recombinant vector (pGMBS) was transformed into Top10 cells (Invitrogen) using standard conditions. Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside), grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al. 1989. Molecular Cloning, A Laboratory Manual. 2nd Edition. Cold Spring Harbor Laboratory Press. Cold Spring Harbor, N.Y.).

Both the pGMBS vector and p1bxSuperGUS vector were digested with XbaI and KpnI (Roche) according to manufacturer's instructions, excising the gentamycin cassette from pGMBS and producing the backbone from the p1bxSuperGUS vector. The resulting fragments were extracted from agarose gel with a QIAquick Gel Extraction Kit (Qiagen) according to manufacturer's instructions. These two fragments were ligated with T4 DNA ligase (Roche) according to manufacturer's instructions.

The resulting recombinant vector (pGMSG) was transformed into Top10 cells (Invitrogen) using standard conditions. Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside) and grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al. 1989. Molecular Cloning, A Laboratory Manual. 2nd Edition. Cold Spring Harbor Laboratory Press. Cold Spring Harbor, N.Y.).

Subcloning of PpAKT-1 into the Binary Vector

The fragment containing the *Physcomitrella* potassium channel (PpAKT-1) was excised from the recombinant PCR2.1 TOPO vector by digestion with SacI and XmaI (Roche) according to manufacture's instructions. The subsequence fragment was excised from agarose gel with a QIAquick Gel Extraction Kit (QIAgen) according to manufacture's instructions and ligated into the binary vectors pGMSG and pGMGG, cleaved with XmaI and SacI and dephosphorylated prior to ligation. As can be seen from FIG. 4, the resulting recombinant binary vector, pBPSLVM001 contained the PpAKT-1 gene in the sense orientation under the constitutive super promoter.

*Agrobacterium* Transformation

The recombinant vector was transformed into *Agrobacterium tumefaciens* C58C1 and PMP90 according to standard conditions (Hoefgen and Willmitzer, 1990). After the transformation single colonies were then picked and inoculated in fresh medium. The presence of the plasmid constructs containing the PpAKT-1 was verified by PCR amplification.

Plant Transformation

*Arabidopsis thaliana* ecotype C24 were grown and transformed according to standard conditions (Bechtold 1993, Acad. Sci. Paris. 316:1194–1199; Bent et al. 1994, Science 265:1856–1860).

Screening of Transformed Plants

T1 seeds were sterilized according to standard protocols (Xiong et al. 1999, Plant Molecular Biology Reporter 17: 159–170). Seeds were plated on ½ MS 0.6% agar supplemented with 1% sucrose, 150 µg/ml gentamycin (Sigma-Aldrich) and 2 µg/ml benomyl (Sigma-Aldrich). Seeds on plates were vernalized for four days at 4° C. The seeds were germinated in a climatic chamber at an air temperature of 22° C. and light intensity of 40 micromol $s^{-1} m^{-2}$ (white light; Philips TL 65W/25 fluorescent tube) and 16 hours light and 8 hours dark day length cycle. Transformed seedlings were selected after 14 days and transferred to ½ MS 0.6% agar plates supplemented with 1% sucrose and allowed to recover for five-seven Drought Tolerance Screening T1 seedlings were transferred to dry, sterile filter paper in a petri dish and allowed to desiccate for two hours at 80% RH (relative humidity) in a Sanyo Growth Cabinet MLR-350H, micromol $s^{-1}$ $m^{-2}$ (white light; Philips TL 65W/25 fluorescent tube). The RH was then decreased to 60% and the seedlings were desiccated further for eight hours. Seedlings were then removed and placed on ½ MS 0.6% agar plates supplemented with 2 µg/ml benomyl and scored after five days.

FIG. 5 shows pictures of an example of the T1 transgenic lines and wild-type plants after the drought stress. As can be seen from the figure, the transgenic lines survived after the treatment. On the other hand, wild-type plants were nearly dead or did not survive. For the drought stress test, 8 individual T1 transgenic lines were tested and 6 of them survived (75% survival rate). Under the same condition, wild-type plants showed much less survival ratio (below 20%). This result clearly indicates that the transgenic lines over-expressing the PpAKT-1 gene acquired drought stress tolerance. It is noteworthy that these analyses were performed with T1 plants, since the results should be better when a homozygous, strong expresser is found.

Salt Tolerance Screening

Seedlings were transferred to filter paper soaked in ½ MS and placed on ½ MS 0.6% agar supplemented with 2 µg/ml benomyl the night before the salt tolerance screening. For the salt tolerance screening, the filter paper with the seedlings was moved to stacks of sterile filter paper, soaked in 50 mM NaCl, in a petri dish. After two hours, the filter paper with the seedlings was moved to stacks of sterile filter paper, soaked with 200 mM NaCl, in a petri dish. After two hours, the filter paper with the seedlings was moved to stacks of sterile filter paper, soaked in 600 mM NaCl, in a petri dish. After 10 hours, the seedlings were moved to petri dishes containing ½ MS 0.6% agar supplemented with 2 µg/ml benomyl. The seedlings were scored after 5 days. The transgenic plants are then screened for their improved salt tolerance demonstrating that transgene expression confers salt tolerance.

Freezing Tolerance Screening

Seedlings were moved to petri dishes containing ½ MS 0.6% agar supplemented with 2% sucrose and 2 µg/ml benomyl. After four days, the seedlings were incubated at 4° C. for 1 hour and then covered with shaved ice. The seedlings were then placed in an Environmental Specialist ES2000 Environmental Chamber and incubated for 3.5 hours beginning at −1.0° C. decreasing −1° C. hour. The seedlings were then incubated at −5.0° C. for 24 hours and then allowed to thaw at 5° C. for 12 hours. The water was poured off and the seedlings were scored after 5 days. The transgenic plants are then screened for their improved cold tolerance demonstrating that transgene expression confers cold tolerance.

Example 8

Detection of the PpAKT-1 Transgene in the Transgenic *Arabidopsis* Lines

One leaf from a wild type and a transgenic *Arabidopsis* plant was homogenized in 250 µl Hexadecyltrimethyl ammonium bromide (CTAB) buffer (2% CTAB, 1.4 M NaCl, 8 mM EDTA and 20 mM Tris pH 8.0) and 1 µl β-mercaptoethanol. The samples were incubated at 60–65° C. for 30 minutes and 250 µl of Chloroform was then added to each sample. The samples were vortexed for 3 minutes and centrifuged for 5 minutes at 18,000×g. The supernatant was taken from each sample and 150 µl isopropanol was added. The samples were incubated at room temperature for 15 minutes, and centrifuged for 10 minutes at 18,000×g. Each pellet was washed with 70% ethanol, dried, and resuspended in 20 µl TE. 4 µl of above suspension was used in a 20 µl PCR reaction using Taq DNA polymerase (Roche Molecular Biochemicals) according to the manufacturer's instructions. The gene specific primers (Forward primer: 5' ACTCCGCATGGGTGTCACCTTTCGA3' (SEQ ID NO:9), Reverse primer: 5'CTTCTCCACCCTCGCAAA-CACGTCA3' (SEQ ID NO:10)) were used for the PCR. Binary vector plasmid with PpAKT-1 gene cloned in was used as positive control, and the wild type C24 genomic DNA was used as negative control in the PCR reactions. 10 µl PCR reaction was analyzed on 0.8% agarose-ethidium bromide gel.

The transgene was successfully amplified from the T1 transgenic lines, but not from the wild-type plants. This result indicated that the T1 transgenic plant contains at least one copy of the PpAKT-1 transgene. There was no indication of existence of the corresponding gene or homolog of the PpAKT-1 which can be amplified in this method in the wild-type plants.

Example 9

Detection of the PpAKT-1 Transgene mRNA in Transgenic *Arabidopsis* Lines

Transgene expression was detected using RT-PCR. Total RNA was isolated from stress-treated T1 plants using a procedure adapted from (Verwoerd et al. 1989. NAR 17:2362). Leaf samples (50–100 mg) were collected and ground to a fine powder in liquid nitrogen. Ground tissue was resuspended in 500 µl of a 80° C., 1:1 mixture, of phenol to extraction buffer (100 mM LiCl, 100 mM Tris pH8, 10 mM EDTA, 1% SDS), followed by brief vortexing to mix. After the addition of 250 µl of chloroform, each sample was vortexed briefly. Samples were then centrifuged for 5 minutes at 12,000×g. The upper aqueous phase was removed to a fresh eppendorf tube. RNA was precipitated by adding $\frac{1}{10}^{th}$ volume 3M sodium acetate and 2 volumes 95% ethanol. Samples were mixed by inversion and placed on ice for 30 minutes. RNA was pelleted by centrifugation at 12,000×g for 10 minutes. The supernatant was removed and pellets briefly air-dried. RNA sample pellets were resuspended in 10 µl DEPC treated water. To remove contaminating DNA from the samples, each was treated with RNase-free DNase (Roche) according to the manufacturer's recommendations. cDNA was synthesized from total RNA using the $1^{st}$ Strand cDNA synthesis kit (Boehringer Mannheim) following manufacturer's recommendations. PCR amplification of a gene-specific fragment from the synthesized cDNA was performed using Taq DNA polymerase (Roche) and gene-specific primers (Forward primer: 5'ACTCCGCATGGGT-GTCACCTTTCGA3' (SEQ ID NO:11) and Reverse primer: 5'CTTCTCCACCCTCGCAAACACGTCA3' (SEQ ID NO:10) designed specifically for PpAKT-1) in the following reaction: 1×PCR buffer, 1.5 mM $MgCl_2$, 0.2 µM each primer, 0.2 µM dNTPs, 1 unit polymerase, 5 µl cDNA from synthesis reaction. Amplification was performed under the following conditions: Denaturation, 95° C., 1 minute; annealing, 62° C., 30 seconds; extension, 72° C., 1 minute, 35 cycles; extension, 72° C., 5 minutes; hold, 4° C., forever. PCR products were run on a 1% agarose gel, stained with ethidium bromide, and visualized under UV light using the Quantity-One gel documentation system (Bio-Rad).

Expression of the transgenes was detected in the T1 transgenic line. This result indicated that the transgenes are expressed in the transgenic lines and strongly suggested that their gene product improved plant stress tolerance in the transgenic lines. In agreement with the previous statement, no expression of identical or very similar endogenous genes could be detected by this method.

Example 10

Engineering Stress-tolerant Soybean Plants by Over-expressing the PpAKT-1 Gene

The construct pBPSLVM001 is used to transform soybean as described below.

Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and resuspended in MS (Murashige and Skoog, 1962) medium supplemented with 100 µM acetosyringone. Bacteria cultures are incubated in this pre-induction medium for 2 hours at room temperature before use. The axes of soybean zygotic seed embryos at approximately 15% moisture content are imbibed for 2 hours at room temperature with the pre-induced *Agrobacterium* suspension culture. The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the agrobacteria. The liquid medium is used to moisten the sterile filter paper. The embryos are incubated for 4 weeks at 25° C., under 150 µmol $m^{-2}$ $sec^{-1}$ and 12 hours photoperiod. Once the seedlings have produced roots, they are transferred to sterile metromix soil. The medium of the in vitro plants is washed off before the plants are transferred to soil. The plants are kept under a plastic cover for 1 week to favor the acclimatization process. Then the plants are transferred to a growth room where they are incubated at 25° C., under 150 µmol $m^{-2}$ $sec^{-1}$ light intensity and 12 hours photoperiod for about 80 days.

The transgenic plants are then screened for their improved drought, salt and/or cold tolerance according to the screening method described in Example 7 demonstrating that transgene expression confers stress tolerance.

Example 11

Engineering Stress-tolerant Corn Plants by Over-expressing the PpAKT-1 Gene

The construct pBPSLVM001 is used to transform corn as described below.

Transformation of maize (*Zea Mays L.*) is performed with the method described by Ishida et al. 1996. Nature Biotch 14745–50. Immature embryos are co-cultivated with *Agrobacterium tumefaciens* that carry "super binary" vectors, and transgenic plants are recovered through organogenesis. This procedure provides a transformation efficiency of between 2.5% and 20%. The transgenic plants are then screened for their improved drought, salt and/or cold tolerance according to the screening method described in Example 7 demonstrating that transgene expression confers stress tolerance.

Example 12

Engineering Stress-tolerant Wheat Plants by Over-expressing the PpAKT-1 Gene

The construct pBPSLVM001 is used to transform wheat as described below.

Transformation of wheat is performed with the method described by Ishida et al. 1996. Nature Biotch 14745–50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are then screened for their improved stress tolerance according to the screening method described in Example 7 demonstrating that transgene expression confers drought tolerance.

Example 13

Identification of Homologous and Heterologous Genes

Gene sequences can be used to identify homologous or heterologous genes from cDNA or genomic libraries. Homologous genes (e. g. full-length cDNA clones) can be isolated via nucleic acid hybridization using for example cDNA libraries. Depending on the abundance of the gene of interest, 100,000 up to 1,000,000 recombinant bacteriophages are plated and transferred to nylon membranes. After denaturation with alkali, DNA is immobilized on the membrane by e. g. UV cross linking. Hybridization is carried out at high stringency conditions. In aqueous solution hybridization and washing is performed at an ionic strength of 1 M NaCl and a temperature of 68° C. Hybridization probes are generated by e. g. radioactive ($^{32}$P) nick transcription labeling (High Prime, Roche, Mannheim, Germany). Signals are detected by autoradiography.

Partially homologous or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homology (or sequence identity/similarity) only to a distinct domain of (for example 10–20 amino acids) the PpAKT-1 protein can be carried out by using synthetic radio labeled oligonucleotide probes. Radiolabeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are then radiolabeled by, for example, nick transcription. Hybridization is normally performed at low stringency conditions using high oligonucleotide concentrations.

Oligonucleotide Hybridization Solution:

6×SSC
0.01 M sodium phosphate
1 mM EDTA (pH 8)
0.5% SDS
100 μg/ml denatured salmon sperm DNA
0.1% nonfat dried milk During hybridization, temperature is lowered stepwise to 5–10° C. below the estimated oligonucleotide Tm or down to room temperature followed by washing steps and autoradiography. Washing is performed with low stringency such as 3 washing steps using 4×SSC. Further details are described by Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons.

Example 14

Identification of Homologous Genes by Screening Expression Libraries with Antibodies C-DNA clones can be used to produce recombinant protein for example in *E. coli* (e. g. Qiagen QIAexpress pQE system). Recombinant proteins are then normally affinity purified via Ni-NTA affinity chromatography (Qiagen). Recombinant proteins are then used to produce specific antibodies for example by using standard techniques for rabbit immunization. Antibodies are affinity purified using a Ni-NTA column saturated with the recombinant antigen as described by Gu et al., 1994 BioTechniques 17:257–262. The antibody can than be used to screen expression cDNA libraries to identify homologous or heterologous genes via an immunological screening (Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons).

Example 15

In Vivo Mutagenesis

In vivo mutagenesis of microorganisms can be performed by passage of plasmid (or other vector) DNA through *E. coli* or other microorganisms (e.g. *Bacillus* spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp, W. D. (1996) DNA repair mechanisms, in: *Escherichia coli* and *Salmonella*, p. 2277–2294, ASM: Washington.) Such strains are well known to those skilled in the art. The use of such strains is illustrated, for example, in Greener, A. and Callahan, M. (1994) Strategies 7: 32–34. Transfer of mutated DNA molecules into plants is preferably done after selection and testing in microorganisms. Transgenic plants are generated according to various examples within the exemplification of this document.

Example 16

In Vitro Analysis of the Function of *Physcomitrella* Genes in Transgenic Organisms The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M., and Webb, E. C., (1979) Enzymes. Longmans: London; Fersht, (1985) Enzyme Structure and Mechanism. Freeman: New York; Walsh, (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, $3^{rd}$ ed. Academic Press: New York; Bisswanger, H., (1994) Enzymkinetik, $2^{nd}$ ed. VCH: Weinheim (ISBN 3527300325); Bergmeyer, H. U., Bergmeyer, J., Graβl, M., eds. (1983–1986) Methods of Enzymatic Analysis, $3^{rd}$ ed., vol. I–XII, Verlag Chemie: Weinheim; and Ullmann's Encyclopedia of Industrial Chemistry (1987) vol. A9, Enzymes. VCH: Weinheim, p. 352–363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al. (1995) *EMBO J.* 14: 3895–3904 and references cited therein). Reporter gene test systems are well known and established for applications in both pro- and eukaryotic cells, using enzymes such as β-galactosidase, green fluorescent protein, and several others.

The determination of activity of membrane-transport proteins can be performed according to techniques such as those described in Gennis, R. B. Pores, Channels and Transporters, in Biomembranes, Molecular Structure and Function, pp. 85–137, 199–234 and 270–322, Springer: Heidelberg (1989).

Example 17

Purification of the Desired Product from Transformed Organisms

Recovery of the desired product from plant material (i.e., *Physcomitrella patents* or *Arabidopsis thaliana*), fungi, algae, ciliates, *C. glutamicum* cells, or other bacterial cells transformed with the nucleic acid sequences described herein, or the supernatant of the above-described cultures can be performed by various methods well known in the art. If the desired product is not secreted from the cells, can be harvested from the culture by low-speed centrifugation, the cells can be lysed by standard techniques, such as mechanical force or sonification. Organs of plants can be separated mechanically from other tissue or organs. Following homogenization cellular debris is removed by centrifugation, and the supernatant fraction containing the soluble proteins is retained for further purification of the desired compound. If the product is secreted from desired cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey, J. E. & Ollis, D. F. Biochemical Engineering Fundamentals, McGraw-Hill: New York (1986). Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994 *Appl. Environ. Microbiol.* 60:133–140; Malakhova et al., 1996 *Biotekhnologiya* 11:27–32; and Schmidt et al., 1998 *Bioprocess Engineer.* 19:67–70. Ulmann's Encyclopedia of Industrial Chemistry, (1996) vol. A27, VCH: Weinheim, p. 89–90, p. 521–540, p. 540–547, p. 559–566, 575–581 and p. 581–587; Michal, G. (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

---

We claim:

1. A transgenic plant transformed with an isolated polynucleotide, wherein expression of the polynucleotide in the plant results in increased tolerance to an environmental stress as compared to a wild type variety of the plant, wherein the isolated polynucleotide encodes a polypeptide having AKT-1 activity and is selected from the group consisting of:
   a) a polynucleotide having nucleotides 1–3020 as set forth in SEQ ID NO:2;
   b) a polynucleotide encoding a polypeptide having amino acids 1–944 as set forth in SEQ ID NO:3;
   c) a polynucleotide having at least 95% sequence identity to the polynucleotide as set forth in SEQ ID NO:2;
   d) a polynucleotide encoding a polypeptide having at least 95% sequence identity to the polypeptide as set forth in SEQ ID NO:3; and
   e) a polynucleotide hybridizing under stringent conditions to either of the polynucleotides of a) or c) above, wherein the stringent conditions comprise hybridization in 6×SSC at about 45° C. followed by one or more washes in 0.2×SSC and 0.1% SDS at 65° C.

2. The transgenic plant of claim 1, wherein the polynucleotide has the sequence as set forth in SEQ ID NO:2.

3. The transgenic plant of claim 1, wherein the polynucleotide has at least 95% sequence identity to the polynucleotide having the sequence as set forth in SEQ ID NO:2.

4. The transgenic plant of claim 1, wherein the polynucleotide encodes the polypeptide having the sequence as set forth in SEQ ID NO:3.

5. The transgenic plant of claim 1, wherein the polynucleotide encodes the polypeptide having AKT-1 activity and at least 95% sequence identity to the polypeptide having the sequence as set forth in SEQ ID NO:3.

6. The transgenic plant of claim 1, wherein the environmental stress is selected from the group consisting of drought, high salinity, and low temperature.

7. The transgenic plant of claim 6, wherein the environmental stress is drought.

8. The transgenic plant of claim 1, wherein the plant is a monocot.

9. The transgenic plant of claim 1, wherein the plant is a dicot.

10. The transgenic plant of claim 1, wherein the plant is selected from the group consisting of maize, wheat, rye, oat, triticale, rice, barley, soybean, peanut, cotton, rapeseed, canola; manihot, pepper, sunflower, tagetes, solanaceous plants, potato, tobacco, eggplant, tomato, Vicia species, pea, alfalfa, coffee, cacao, tea, Salix species, oil palm, coconut, perennial grass and a forage crop plant.

11. A transgenic seed comprising a transgene, wherein the seed is true breeding for increased tolerance to environmental stress as compared to a wild type variety of the seed, wherein the transgene comprises a polynucleotide encoding a polypeptide having AKT-1 activity, wherein the polynucleotide is selected from the group consisting of:
   a) a polynucleotide having nucleotides 1–3020 as set forth in SEQ ID NO:2;
   b) a polynucleotide encoding a polypeptide having amino acids 1–944 as set forth in SEQ ID NO:3;
   c) a polynucleotide having at least 95% sequence identity to the polynucleotide as set forth in SEQ ID NO:2;
   d) a polynucleotide encoding the polypeptide having at least 95% sequence identity to the polypeptide as set forth in SEQ ID NO:3; and
   e) a polynucleotide hybridizing under stringent conditions to either of the polynucleotides of a) or c) above, wherein the stringent conditions comprise hybridization in 6×SSC at about 45° C. followed by one or more washes in 0.2×SSC and 0.1% SDS at 65° C.

12. The transgenic seed of claim 11, wherein the polynucleotide has the sequence as set forth in SEQ ID NO:2.

13. The transgenic seed of claim 11, wherein the polynucleotide has at least 95% sequence identity to the polynucleotide having the sequence as set forth in SEQ ID NO:2.

14. The transgenic seed of claim 11, wherein the polynucleotide encodes the polypeptide having the sequence as set forth in SEQ ID NO:3.

15. The transgenic seed of claim 11, wherein the polynucleotide encodes the polypeptide having at least 95% sequence identity to the polypeptide having the sequence as set forth in SEQ ID NO:3.

16. An isolated polynucleotide encoding a polypeptide haying AKT-1 activity, wherein the polynucleotide is selected from the group consisting of:
   a) a polynucleotide having nucleotides 1–3020 as set forth in SEQ ID NO:2;
   b) a polynucleotide encoding a polypeptide having amino acids 1–944 as set forth in SEQ ID NO:3;
   c) a polynucleotide having at least 95% sequence identity to the polynucleotide as set forth in SEQ ID NO:2;
   d) a polynucleotide encoding a polypeptide having at least 95% sequence identity to the polypeptide as set forth in SEQ ID NO:3; and
   e) a polynucleotide hybridizing under stringent conditions to either of the polynucleotides of a) or c) above, wherein the stringent conditions comprise hybridization in 6×SSC at about 45° C. followed by one or more washes in 0.2×SSC and 0.1% SDS at 65° C.

17. The isolated polynucleotide of claim 16, wherein the polynucleotide has the sequence as set forth in SEQ ID NO:2.

18. The isolated nucleic acid of claim 16, wherein the polynucleotide has at least 95% sequence identity to the polynucleotide having the sequence as set forth in SEQ ID NO:2.

19. The isolated polynucleotide of claim 16, wherein the polynucleotide encodes the polypeptide having the sequence as set forth in SEQ ID NO:3.

20. The isolated polynucleotide of claim 16, wherein the polynucleotide encodes the polypeptide having at least 95% sequence identity to the polypeptide having the sequence as set forth in SEQ ID NO:3.

21. An expression vector comprising a regulatory sequence operably linked to a polynucleotide, wherein the polynucleotide encodes a polypeptide having AKT-1 activity, and wherein the polynucleotide is selected from the group consisting of:
    a) a polynucleotide having nucleotides 1–3020 as set forth in SEQ ID NO:2;
    b) a polynucleotide encoding a polypeptide having amino acids 1–944 as set forth in SEQ ID NO:3;
    c) a polynucleotide having at least 95% sequence identity to the polynucleotide as set forth in SEQ ID NO:2;
    d) a polynucleotide encoding a polypeptide having at least 95% sequence identity to the polypeptide as set forth in SEQ ID NO:3; and
    e) a polynucleotide hybridizing under stringent conditions to either of the polynucleotides of a) or c) above, wherein the stringent conditions comprise hybridization in 6×SSC at about 45° C. followed by one or more washes in 0.2×SSC and 0.1% SDS at 65° C.

22. A method of producing a transgenic plant comprising a polynucleotide encoding a polypeptide having AKT-1 activity, wherein the plant has an increased tolerance to an environmental stress as compared to a wild type variety of the plant, the method comprising the steps of, transforming a plant cell with an expression vector comprising a regulatory sequence operably linked to the polynucleotide; and generating the transgenic plant from the plant cell, wherein the polynucleotide encoding a polypeptide having AKT-1 activity is selected from the group consisting of:
    a) a polynucleotide having nucleotides 1–3020 as set forth in SEQ ID NO:2;
    b) a polynucleotide encoding a polypeptide having amino acids 1–944 as set forth in SEQ ID NO:3;
    c) a polynucleotide having at least 95% sequence identity to the polynucleotide as set forth in SEQ ID NO:2;
    d) a polynucleotide encoding a polypeptide having at least 95% sequence identity to the polypeptide as set forth in SEQ ID NO:3; and
    e) a polynucleotide hybridizing under stringent conditions to either of the polynucleotides of a) or c) above, wherein the stringent conditions comprise hybridization in 6×SSC at about 45° C. followed by one or more washes in 0.2×SSC and 0.1% SDS at 65° C.

23. The method of claim 22, wherein the polynucleotide has the sequence as set forth in SEQ ID NO:2.

24. The method of claim 22, wherein the polynucleotide has at least 95% sequence identity to the polynucleotide having the sequence as set forth in SEQ ID NO:2.

25. The method of claim 22, wherein the polynucleotide encodes the polypeptide having the sequence as set forth in SEQ ID NO:3.

26. The method of claim 22, wherein the polynucleotide encodes the polypeptide having at least 95% sequence identity to the polypeptide having the sequence as set forth in SEQ ID NO:3.

27. The method of claim 22, wherein the regulatory sequence is a promoter.

28. The method of claim 27, wherein the promoter is tissue specific.

29. The method of claim 27, wherein the promoter is developmentally regulated.

* * * * *

SEQUENCE LISTING

```
<160> NUMBER OF SEQ ID NOS: 11

<210> SEQ ID NO 1
<211> LENGTH: 697
<212> TYPE: DNA
<213> ORGANISM: Physcomitrella patens

<400> SEQUENCE: 1
gcacgagcag atgaaggctg agtcacttcg gaagtgcagt gatcgtctct gtttctgagg      60
```

-continued

| | |
|---|---|
| aatatttatc gtacagtgct cgttttgttg aactcgtctt tatgtcttgg tcgcgaagcc | 120 |
| ttccgtgacg cggatttgat agcagttttg cagctcactg gtaggagcg ttcttcacgc | 180 |
| tcatggtttc agtttggatg ttgtcgctgg ctttagattg cctttggacg atgactcaat | 240 |
| tcggtgaaaa ttcgataagt tgcgtttcgt agtgagcagt ctcccagagg aatctgccat | 300 |
| tgtgtagcga ggtgtaggat catggggtgg tcggtaagcg ggttgaccca caaggtcctt | 360 |
| ggagcagtgg ggctgatgaa gtacggcaat cagcgcaagg cctctacccc cagcatcttc | 420 |
| agccatgcat acagcagcgg aatgttgccg gctcttggat ccaaccagag tacgaagaac | 480 |
| gtccttcaaa agaaatacgt tattcatcct acaacaaga attacaggta ctggcagggg | 540 |
| attttggtgg tgctagtgtt ttactccgca tgggtgtcac ctttcgagtt tgggttcgtg | 600 |
| caaaatcctc gcggtgctct gttaactgtc gacaatattg tcaactttct cttcttcatc | 660 |
| gacatcgtat tgaccttctt cgtcgcgtat ctcgaca | 697 |

<210> SEQ ID NO 2
<211> LENGTH: 3020
<212> TYPE: DNA
<213> ORGANISM: Physcomitrella patens

<400> SEQUENCE: 2

| | |
|---|---|
| gaattcgccc ttatcccggg cgtttcgtag tgagcagtct cccagaggaa tctgccattg | 60 |
| tgtagcgagg tgtaggatca tggggtggtc ggtaagcggg ttgacccaca aggtccttgg | 120 |
| agcagtgggg ctgatgaagt acggcaatca gcgcaaggcc tctacccca gcatcttcag | 180 |
| ccatgcatac agcagcggaa tgttgccggc tcttggatcc aaccagagta cgaagaacgt | 240 |
| ccttcaaaag aaatacgtta ttcatcctta caacaagaat acaggtact ggcaggggat | 300 |
| tttggtggtg ctagtgtttt actccgcatg gtgtcacct ttcgagtttg gttcgtgca | 360 |
| aaatcctcgc ggtgctctgt taactgtcga acatattgtc aactttctct cttcatcga | 420 |
| catcgtattg accttcttcg tcgcgtatct cgacacctca actttttga tggaagacaa | 480 |
| cttgaagaag atcgccatca ggtatttgag aacatggttt attttggatg ttgtgtcgac | 540 |
| tgttccattg gccgcagtaa tagcgatttt cactggaaaa tatgagacag ggtttgcggc | 600 |
| cagttttgtc aatttgttgc gcctctggcg attgcgccgt gtgagtgacg tgtttgcgag | 660 |
| ggtggagaag aatgtgaaat ttagttactt ctggactcga tgcctcaaac tctttctggt | 720 |
| gactgtgttt gtttgccact tgcggcctc ctcgtactac ttattggctg ctcgacatcc | 780 |
| ggcaagcaaa gaggcagata cgtggctagg agctgtgctc ccaaattta aagaggagtc | 840 |
| actgtgggcg cggtacgtga cgagtatgta ctggtccatc actacactgg cgactgtggg | 900 |
| atatggcgat ttgcatccag tcaaccgtgg tgaaatgatc ttcaccatcc tttacatgtt | 960 |
| gctgaatctg gcattgactg cgtacatcat aggaaacatg accaatctca tcactcgtct | 1020 |
| taccgcacga actcgtgact atcgtgactc ggtgcaacaa ttggtggagt ttgcaactag | 1080 |
| aaatcagttg ccacgcaagc ttcacgagca atgatctcc cacgtgcagc tcaagttcaa | 1140 |
| gacagagagc cttcagcatc aagggaccat agccaccta ccaaaggcta tccgctcatc | 1200 |
| tgttgcgcaa tttctgtttt taacacagt cgagaaagtg tacctttcc aaggcacttc | 1260 |
| ttacaatttt cgtactcagc tggtgtcgga tgaaggtc gagttcttcc ctcctcgcga | 1320 |
| ggaaattatt ctggttaacg aggcccctc cgagttttac atagttgtga atggttccgc | 1380 |
| ggatgtaata attcgaaggg aggaagccgg atcagagcaa attctaatga cggctcaggc | 1440 |
| aactgatgta attggcgaga tagggtgat ttgttacagg ccacagcctt tcactgtgcg | 1500 |

-continued

```
aagtcgaaag ttatcccagc tcttgcgact tgaccgcatt gtgtttatga acattgtgca   1560
acaatacaag gaagacggcc agaagattgt tgacaatctg ttgcagcgct tgcgagaagc   1620
ctatgatcct cgatttgagg agcttttcctc tgagattgaa gccctccttg ttgaaggcgg   1680
cgaaatatcg gaaccaagcg tatgtgcggt tgctgccgga ggaaatgtgg aggttatgca   1740
gcagctgttg agcaaaggcg cggaggtgga caagacagat tatcacgtc ggactgctct    1800 ggtcattgca tcatcaaaag gttacgagga gtgcgtcaag ctccttctgg aacacggagc   1860
tgaccccaac aaggctgatg tgtatgggaa ggttcctcta cttgaggccc ttattgcccg   1920
cgacacggct accgtgaagc tcttatcaga gaacggggcg accttgaaaa atgcggacat   1980
gggggtatac ctcgggcaag ctgtgctcga ctgtaatcga gacctcattg acgactactt   2040
aaaatatgga accgacataa acacagcagg cgaatctgaa ggactgagtg cgctccacat   2100
tgctgttatt gatggcaaca tggatatggt gaggtttta gtatcccgag gagccgaccc    2160
tcacatcaag cctggtgatg aggccaccct taccgcatac gagctagctg agagaagtgc   2220
agatcacccc gaaatagctt cctttttgaa ggcccaatca gtccgcgatg aaccatacag   2280
ttccatcacg cctagagagt cgacatctaa cgcaaatcag aagaggcttc caaggaaggg   2340
aagctccaat gttgaattcc agattgatga ggtaacaccc ccgcctagtc aaataaagg    2400 attttccgga gagcgaacga tacactcatt aatgcgaaag cagtcggctc ggggccgtct   2460
catgactata agaggacaga aaaccctcag ccggcaacta aacgcaaacc agaacccttc   2520 aggttgggc ttgagacggc gtgacaatcg agaccctctt cagactttc catcagctgg     2580 cgctgctaag gaggttcctc ttcgtgtcat catccattct tatcatcctt ggaacaagga   2640
agcggtggga cttggaaagg tcgttttgct gccgaaaact attgaagagg ttctcaagat   2700
tgcgaacgag aaattcaaca atcatccaac gaaggtgttg aacaaagagg cagctgagat   2760
tgacgacttg agtgtcatcc gagaaaacga caacttgtat gtcattaacg attcagagaa   2820
gttgaacacg agttccccccc cagggatgga cacagatgac ctcatagcaa gattgcaagc   2880
aatagtcaca gcattgtctc aacccaaacc atagactcat gcatgcgacc aaggttgggt    2940
atgtacttct cataagctta ggactcgact taggatatca cgagatcagc gacagtgtct   3000
gagctcgcaa gggcgaattc                                              3020
```

<210> SEQ ID NO 3
<211> LENGTH: 944
<212> TYPE: PRT
<213> ORGANISM: Physcomitrella patens

<400> SEQUENCE: 3

```
Met Gly Trp Ser Val Ser Gly Leu Thr His Lys Val Leu Gly Ala Val
 1               5                  10                  15

Gly Leu Met Lys Tyr Gly Asn Gln Arg Lys Ala Ser Thr Pro Ser Ile
            20                  25                  30

Phe Ser His Ala Tyr Ser Ser Gly Met Leu Pro Ala Leu Gly Ser Asn
        35                  40                  45

Gln Ser Thr Lys Asn Val Leu Gln Lys Lys Tyr Val Ile His Pro Tyr
    50                  55                  60

Asn Lys Asn Tyr Arg Tyr Trp Gln Gly Ile Leu Val Val Leu Val Phe
65                  70                  75                  80

Tyr Ser Ala Trp Val Ser Pro Phe Glu Phe Gly Phe Val Gln Asn Pro
                85                  90                  95
```

-continued

```
Arg Gly Ala Leu Leu Thr Val Asp Asn Ile Val Asn Phe Leu Phe Phe
            100                 105                 110
Ile Asp Ile Val Leu Thr Phe Val Ala Tyr Leu Asp Thr Ser Thr
        115                 120                 125
Phe Leu Met Glu Asp Asn Leu Lys Lys Ile Ala Ile Arg Tyr Leu Arg
        130                 135                 140
Thr Trp Phe Ile Leu Asp Val Val Ser Thr Val Pro Leu Ala Ala Val
145                 150                 155                 160
Ile Ala Ile Phe Thr Gly Lys Tyr Glu Thr Gly Phe Ala Ala Ser Phe
                165                 170                 175
Val Asn Leu Leu Arg Leu Trp Arg Leu Arg Arg Val Ser Asp Val Phe
            180                 185                 190
Ala Arg Val Glu Lys Asn Val Lys Phe Ser Tyr Phe Trp Thr Arg Cys
        195                 200                 205
Leu Lys Leu Phe Leu Val Thr Val Phe Val Cys His Phe Ala Ala Cys
    210                 215                 220
Ser Tyr Tyr Leu Leu Ala Ala Arg His Pro Ala Ser Lys Glu Ala Asp
225                 230                 235                 240
Thr Trp Leu Gly Ala Val Leu Pro Asn Phe Lys Glu Glu Ser Leu Trp
                245                 250                 255
Ala Arg Tyr Val Thr Ser Met Tyr Trp Ser Ile Thr Thr Leu Ala Thr
            260                 265                 270
Val Gly Tyr Gly Asp Leu His Pro Val Asn Arg Gly Glu Met Ile Phe
        275                 280                 285
Thr Ile Leu Tyr Met Leu Leu Asn Leu Ala Leu Thr Ala Tyr Ile Ile
    290                 295                 300
Gly Asn Met Thr Asn Leu Ile Thr Arg Leu Thr Ala Arg Thr Arg Asp
305                 310                 315                 320
Tyr Arg Asp Ser Val Gln Gln Leu Val Glu Phe Ala Thr Arg Asn Gln
                325                 330                 335
Leu Pro Arg Lys Leu His Glu Gln Met Ile Ser His Val Gln Leu Lys
            340                 345                 350
Phe Lys Thr Glu Ser Leu Gln His Gln Gly Thr Ile Ala Thr Leu Pro
        355                 360                 365
Lys Ala Ile Arg Ser Ser Val Ala Gln Phe Leu Phe Phe Asn Thr Val
    370                 375                 380
Glu Lys Val Tyr Leu Phe Gln Gly Thr Ser Tyr Asn Phe Arg Thr Gln
385                 390                 395                 400
Leu Val Ser Glu Met Lys Val Glu Phe Phe Pro Arg Glu Glu Ile
                405                 410                 415
Ile Leu Val Asn Glu Ala Pro Ser Glu Phe Tyr Ile Val Val Asn Gly
            420                 425                 430
Ser Ala Asp Val Ile Arg Arg Glu Glu Ala Gly Ser Glu Gln Ile
        435                 440                 445
Leu Met Thr Ala Gln Ala Thr Asp Val Ile Gly Glu Ile Gly Val Ile
    450                 455                 460
Cys Tyr Arg Pro Gln Pro Phe Thr Val Arg Ser Arg Lys Leu Ser Gln
465                 470                 475                 480
Leu Leu Arg Leu Asp Arg Ile Val Phe Met Asn Ile Val Gln Gln Tyr
                485                 490                 495
Lys Glu Asp Gly Gln Lys Ile Val Asp Asn Leu Leu Gln Arg Leu Arg
            500                 505                 510
Glu Ala Tyr Asp Pro Arg Phe Glu Glu Leu Ser Ser Glu Ile Glu Ala
```

-continued

```
                515                 520                 525
Leu Leu Val Glu Gly Gly Glu Ile Ser Glu Pro Ser Val Cys Ala Val
        530                 535                 540
Ala Ala Gly Gly Asn Val Glu Val Met Gln Gln Leu Leu Ser Lys Gly
545                 550                 555                 560
Ala Glu Val Asp Lys Thr Asp Tyr His Gly Arg Thr Ala Leu Val Ile
                565                 570                 575
Ala Ser Ser Lys Gly Tyr Glu Cys Val Lys Leu Leu Leu Glu His
                580                 585                 590
Gly Ala Asp Pro Asn Lys Ala Asp Val Tyr Gly Lys Val Pro Leu Leu
                595                 600                 605
Glu Ala Leu Ile Ala Arg Asp Thr Ala Thr Val Lys Leu Leu Ser Glu
        610                 615                 620
Asn Gly Ala Thr Leu Lys Asn Ala Asp Met Gly Val Tyr Leu Gly Gln
625                 630                 635                 640
Ala Val Leu Asp Cys Asn Arg Asp Leu Ile Asp Tyr Leu Lys Tyr
                645                 650                 655
Gly Thr Asp Ile Asn Thr Ala Gly Glu Ser Glu Gly Leu Ser Ala Leu
                660                 665                 670
His Ile Ala Val Ile Asp Gly Asn Met Asp Met Val Arg Phe Leu Val
                675                 680                 685
Ser Arg Gly Ala Asp Pro His Ile Lys Pro Gly Asp Glu Ala Thr Leu
        690                 695                 700
Thr Ala Tyr Glu Leu Ala Glu Arg Ser Ala Asp His Pro Glu Ile Ala
705                 710                 715                 720
Ser Phe Leu Lys Ala Gln Ser Val Arg Asp Glu Pro Tyr Ser Ser Ile
                725                 730                 735
Thr Pro Arg Glu Ser Thr Ser Asn Ala Asn Gln Lys Arg Leu Pro Arg
                740                 745                 750
Lys Gly Ser Ser Asn Val Glu Phe Gln Ile Asp Glu Val Thr Pro Pro
                755                 760                 765
Pro Ser Pro Asn Lys Gly Phe Ser Gly Glu Arg Thr Ile His Ser Leu
        770                 775                 780
Met Arg Lys Gln Ser Ala Arg Gly Arg Leu Met Thr Ile Arg Gly Gln
785                 790                 795                 800
Lys Thr Leu Ser Arg Gln Leu Asn Ala Asn Gln Asn Pro Ser Gly Trp
                805                 810                 815
Gly Leu Arg Arg Arg Asp Asn Arg Asp Pro Leu Gln Thr Phe Pro Ser
                820                 825                 830
Ala Gly Ala Ala Lys Glu Val Pro Leu Arg Val Ile Ile His Ser Tyr
                835                 840                 845
His Pro Trp Asn Lys Glu Ala Val Gly Leu Gly Lys Val Val Leu Leu
        850                 855                 860
Pro Lys Thr Ile Glu Glu Val Leu Lys Ile Ala Asn Glu Lys Phe Asn
865                 870                 875                 880
Asn His Pro Thr Lys Val Leu Asn Lys Glu Ala Ala Glu Ile Asp Asp
                885                 890                 895
Leu Ser Val Ile Arg Glu Asn Asp Asn Leu Tyr Val Ile Asn Asp Ser
                900                 905                 910
Glu Lys Leu Asn Thr Ser Ser Pro Pro Gly Met Asp Thr Asp Asp Leu
        915                 920                 925
Ile Ala Arg Leu Gln Ala Ile Val Thr Ala Leu Ser Gln Pro Lys Pro
930                 935                 940
```

```
<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 4
caggaaacag ctatgacc                                                  18

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 5
ctaaagggaa caaaagctg                                                 19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
tgtaaaacga cggccagt                                                  18

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 7
atcccgggcg tttcgtagtg agcagtctcc ca                                  32

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 8
gcgagctcag acactgtcgc tgatctcgtg at                                  32

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 9
actccgcatg ggtgtcacct ttcga                                          25

<210> SEQ ID NO 10
<211> LENGTH: 25
<212> TYPE: DNA
<213> ORGANISM: Artificial Sequence
<220> FEATURE:
```

```
<223> OTHER INFORMATION: Description of Artificial Sequence: Primer

<400> SEQUENCE: 10
cttctccacc ctcgcaaaca cgtca                                            25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 11
actccgcatg ggtgtcacct ttcga                                            25
```